United States Patent
Moravec et al.

(10) Patent No.: US 12,352,697 B2
(45) Date of Patent: Jul. 8, 2025

(54) AIR BUBBLE SENSING SYSTEMS AND RELATED SIGNAL PROCESSING

(71) Applicant: Donaldson Company, Inc., Bloomington, MN (US)

(72) Inventors: Davis B. Moravec, Burnsville, MN (US); Michael J. Cronin, Apple Valley, MN (US); Danny W. Miller, Ackley, IA (US); Chad M. Goltzman, Bloomington, MN (US); Mikayla A. Yoder, Eagan, MN (US); Bradly G. Hauser, Minneapolis, MN (US)

(73) Assignee: Donaldson Company, Inc., Bloomington, MN (US)

( * ) Notice: Subject to any disclaimer, the term of this patent is extended or adjusted under 35 U.S.C. 154(b) by 169 days.

(21) Appl. No.: 18/115,464

(22) Filed: Feb. 28, 2023

(65) Prior Publication Data
US 2023/0296529 A1    Sep. 21, 2023

Related U.S. Application Data

(60) Provisional application No. 63/320,557, filed on Mar. 16, 2022.

(51) Int. Cl.
  *G01N 21/84*     (2006.01)
  *F04B 53/20*     (2006.01)
(52) U.S. Cl.
  CPC ............ *G01N 21/84* (2013.01); *F04B 53/20* (2013.01); *G01N 2021/8405* (2013.01)

(58) Field of Classification Search
  CPC .......... G01N 2021/6421; G01N 21/33; G01N 21/645; G01N 2201/061;
  (Continued)

(56) References Cited

U.S. PATENT DOCUMENTS

| | | | |
|---|---|---|---|
| 4,638,305 | A | 1/1987 | Sutton |
| 5,033,858 | A | 7/1991 | Twerdochlib et al. |

(Continued)

FOREIGN PATENT DOCUMENTS

| | | |
|---|---|---|
| CN | 101715545 | 5/2010 |
| CN | 101965447 | 2/2011 |

(Continued)

OTHER PUBLICATIONS

"Final Office Action," for U.S. Appl. No. 17/496,385 mailed Dec. 13, 2023 (31 pages).

(Continued)

*Primary Examiner* — Michael P Stafira
(74) *Attorney, Agent, or Firm* — Pauly, DeVries Smith & Deffner LLC

(57) ABSTRACT

Embodiments herein relate to systems for detecting air bubbles in fluids. In an embodiment, a fluid system aeration detector is included having an optical air bubble sensor. The optical air bubble sensor can include a light source, a light detector, and a sensor controller. The sensor controller can be in signal communication with the light detector and can be configured to detect air bubbles based on the signals received from the light detector. The sensor controller can further be configured to estimate an amount of aeration of a fluid based on the detected air bubbles. Other embodiments are also included herein.

16 Claims, 14 Drawing Sheets

(58) Field of Classification Search
CPC ... G01N 2021/6417; G01N 2021/1734; G01N 2021/6491; G01N 2201/127; G01N 33/18; G01N 15/1434; G01N 21/31; G01N 2021/3137; G01N 2021/8427; G01N 21/314; G01N 21/64; G01N 21/8422; G01N 2201/064; G01N 15/06; G01N 15/075; G01N 15/1459; G01N 15/147; G01N 2015/0046; G01N 21/03; G01N 21/0303; G01N 21/55; G01N 21/65; G01N 1/31; G01N 15/0205; G01N 15/0227; G01N 15/1433; G01N 2015/0038; G01N 2015/0053; G01N 2015/0092; G01N 2015/0238; G01N 2015/0687; G01N 2015/1438; G01N 2015/1486; G01N 2021/556; G01N 2021/6471; G01N 21/255; G01N 21/3504; G01N 21/53; G01N 21/59; G01N 21/87; G01N 2201/0636; G01N 2201/0846; G01N 25/68; G01N 15/01; G01N 15/0211; G01N 15/088; G01N 15/1404; G01N 15/1429; G01N 15/1436; G01N 2015/0011; G01N 2015/0026; G01N 2015/1006; G01N 2015/1402; G01N 2015/144; G01N 2015/145; G01N 2015/1493; G01N 2021/1795; G01N 2021/3513; G01N 2021/4707; G01N 2021/4709; G01N 2021/4735; G01N 2021/4773; G01N 2021/6478; G01N 2021/6482; G01N 21/01; G01N 21/274; G01N 21/45; G01N 21/4738; G01N 21/474; G01N 21/4795; G01N 21/532; G01N 21/538; G01N 21/6428; G01N 21/6452; G01N 21/80; G01N 21/85; G01N 21/94; G01N 2201/0633; G01N 2201/0634; G01N 2201/065; G01N 2201/0668; G01N 2201/08; G01N 2201/12746; G01N 23/04; G01N 23/12; G01N 33/0027; G01N 33/0036; G01N 33/28; G01N 33/2823; G01N 33/502; G01N 33/5061; G01N 33/5073; G01N 33/5076; G01N 33/533; G01N 33/535; G01N 33/54313; G01N 33/5432; G01N 33/54326; G01N 33/54333; G01N 33/5438; G01N 33/54388; G01N 33/582; G01N 33/66; G01N 35/1095; G01N 33/53; G01N 21/648; G01N 27/4473; G01N 27/44743; G01N 27/44791; G01N 15/1012; G01N 27/026; G01N 15/149; G01N 27/447; G01N 30/02; G01N 15/1427; G01N 2015/1406; G01N 21/658; G01N 21/7743; G01N 2027/222; G01N 2035/1025; G01N 21/552; G01N 27/02; G01N 27/221; G01N 27/4145; G01N 27/624; G01N 27/72; G01N 30/7233; G01N 33/54373; G01N 35/1009; G01N 35/10116; G01N 11/02; G01N 2030/027; G01N 27/44795; G01N 15/1023; G01N 2015/1497; G01N 21/05; G01N 21/47; G01N 21/76; G01N 22/00; G01N 25/18; G01N 27/127; G01N 27/26; G01N 27/3272; G01N 27/44747; G01N 33/54306; G01N 33/54366; G01N 33/6842; G01N 33/6872; G01N 1/2273; G01N 1/2813; G01N 15/1031; G01N 15/12; G01N 2001/002; G01N 2001/2223; G01N 2015/1014; G01N 2015/1016; G01N 2015/1027; G01N 2015/1443; G01N 2015/1447; G01N 2015/1452; G01N 2015/1477; G01N 2021/0346; G01N 2030/324; G01N 2030/326; G01N 2030/524; G01N 2030/8804; G01N 2030/8813; G01N 2030/8831; G01N 2035/00108; G01N 2035/00158; G01N 21/554; G01N 21/6456; G01N 2291/0422; G01N 27/06; G01N 27/08; G01N 27/3271; G01N 27/3274; G01N 27/416; G01N 27/4166; G01N 27/622; G01N 30/32; G01N 30/461; G01N 30/463; G01N 30/72; G01N 30/82; G01N 30/8624; G01N 30/8651; G01N 33/0031; G01N 33/6803; G01N 33/6818; G01N 35/00029; G01N 15/02; G01N 15/0255; G01N 15/0266; G01N 15/13; G01N 15/131; G01N 15/134; G01N 15/1484; G01N 19/02; G01N 2015/1024; G01N 2015/1028; G01N 2015/103; G01N 2015/135; G01N 2015/139; G01N 2021/435; G01N 2021/6439; G01N 2021/945; G01N 21/43; G01N 21/6458; G01N 21/66; G01N 21/7703; G01N 21/9501; G01N 21/956; G01N 2201/0228; G01N 2201/06113; G01N 2291/011; G01N 2291/015; G01N 2291/02416; G01N 2291/02845; G01N 2291/0421; G01N 2291/0428; G01N 2291/044; G01N 2291/045; G01N 2291/048; G01N 2291/102; G01N 2291/104; G01N 2291/2675; G01N 24/08; G01N 27/023; G01N 27/3277; G01N 27/44; G01N 27/44739; G01N 2800/32; G01N 29/02; G01N 29/024; G01N 29/032; G01N 29/036; G01N 29/11; G01N 29/222; G01N 29/2456; G01N 29/343; G01N 29/348; G01N 29/46; G01N 30/8644; G01N 33/48707; G01N 33/49; G01N 33/5002; G01N 33/5014

See application file for complete search history.

(56) References Cited

U.S. PATENT DOCUMENTS

| | | | |
|---|---|---|---|
| 5,078,901 | A | 1/1992 | Sparrow |
| 5,388,629 | A | 2/1995 | Kami |
| 5,880,674 | A | 3/1999 | Ufkes et al. |
| 6,260,004 | B1 | 7/2001 | Hays et al. |
| 8,461,519 | B2 | 6/2013 | Lievois et al. |
| 8,473,185 | B2 | 6/2013 | Suwa et al. |
| 8,781,673 | B2 | 7/2014 | Nunn et al. |
| 8,873,060 | B2 | 10/2014 | Webb et al. |
| 9,518,913 | B2 | 12/2016 | Wilhelm |
| 11,131,627 | B2 * | 9/2021 | Bachalo ............... G01N 15/06 |
| 12,210,009 | B2 | 1/2025 | Goltzman et al. |
| 2003/0085180 | A1 | 5/2003 | Akins et al. |
| 2008/0121026 | A1 | 5/2008 | Verdegan |
| 2008/0237503 | A1 | 10/2008 | Albertson |
| 2009/0038406 | A1 | 2/2009 | Hocker |
| 2009/0050809 | A1 | 2/2009 | Holec |
| 2009/0101822 | A1 | 4/2009 | Mitra et al. |
| 2009/0241672 | A1 | 10/2009 | Gysling |
| 2010/0134304 | A1 | 6/2010 | Weinstein et al. |
| 2012/0027630 | A1 | 2/2012 | Forsberg et al. |

(56) References Cited

U.S. PATENT DOCUMENTS

| | | | |
|---|---|---|---|
| 2012/0046848 | A1 | 2/2012 | Suwa et al. |
| 2012/0223515 | A1 | 9/2012 | Avramescu et al. |
| 2012/0312530 | A1 | 12/2012 | Pope et al. |
| 2014/0047827 | A1 | 2/2014 | Maoued et al. |
| 2014/0216602 | A1 | 8/2014 | Kastner et al. |
| 2014/0268156 | A1 | 9/2014 | Smythe et al. |
| 2014/0331742 | A1 | 11/2014 | Campbell et al. |
| 2015/0021482 | A1 | 1/2015 | Mller et al. |
| 2015/0276589 | A1 | 10/2015 | Wagner et al. |
| 2016/0011100 | A1 | 1/2016 | Cipullo et al. |
| 2016/0258870 | A1* | 9/2016 | Tokhtuev ............... G01N 21/85 |
| 2017/0329355 | A1 | 11/2017 | Kanade |
| 2017/0356838 | A1 | 12/2017 | Knollenberg et al. |
| 2019/0242814 | A1 | 8/2019 | Bachalo |
| 2020/0400544 | A1 | 12/2020 | Etschmaier et al. |
| 2020/0400559 | A1 | 12/2020 | Martensson et al. |
| 2021/0223154 | A1 | 7/2021 | Moravec et al. |
| 2021/0310942 | A1 | 10/2021 | Jones et al. |
| 2022/0107303 | A1 | 4/2022 | Goltzman et al. |

FOREIGN PATENT DOCUMENTS

| | | | | |
|---|---|---|---|---|
| CN | 102373987 | | 3/2012 | |
| CN | 103576640 | | 2/2014 | |
| CN | 108374695 | | 8/2018 | |
| CN | 107807402 B | * | 8/2020 | ........... A61M 1/1658 |
| EP | 2869057 A1 | * | 5/2015 | ........ G01N 15/0205 |
| EP | 3698826 A1 | * | 8/2020 | ........ A61M 1/1522 |
| EP | 3745096 A1 | * | 12/2020 | ........ A61B 5/0261 |
| GB | 2568089 | | 5/2019 | |
| JP | S60161546 A | * | 8/1985 | |
| JP | 2010053691 | | 3/2010 | |
| JP | 2010053691 A | * | 3/2010 | |
| JP | 2010528319 | | 8/2010 | |
| JP | 2017223672 | | 12/2017 | |
| KR | 20060041569 | | 5/2006 | |
| KR | 20230133468 A | * | 9/2023 | |
| WO | 2008147408 | | 12/2008 | |
| WO | 2010111231 | | 9/2010 | |
| WO | WO-2013185023 A1 | * | 12/2013 | ......... G01N 15/1012 |
| WO | WO-2019108731 A1 | * | 6/2019 | |
| WO | 2019232305 | | 12/2019 | |
| WO | 2021003346 | | 1/2021 | |
| WO | 2022076747 | | 4/2022 | |
| WO | 2023177728 | | 9/2023 | |

OTHER PUBLICATIONS

"First Office Action," for Chinese Patent Application No. 202080045491.5 mailed Aug. 11, 2023 (30 pages) with English Translation.

"International Search Report and Written Opinion," for PCT Application No. PCT/US2023/015280 mailed Jul. 14, 2023 (13 pages).

"Non-Final Office Action," for U.S. Appl. No. 17/496,385 mailed Aug. 3, 2023 (34 pages).

"Response to Non Final Office Action," for U.S. Appl. No. 17/496,385, filed Nov. 2, 2023 (12 pages).

"Elveflow Microfluidic Bubble Detector Product Information," from Elveflow 2021 Product Catalog. Accessible at URL <elveflow.com/microfluidic-flow-control-products/microfluidic-flow-control-module/microfluidic-liquid-sensor/> (2 pages).

"International Preliminary Report on Patentability," for PCT Application No. PCT/US2020/040625 mailed Jan. 13, 2022 (9 pages).

"International Search Report and Written Opinion," for PCT Application No. PCT/US2020/040625 mailed Oct. 26, 2020 (13 pages).

"International Search Report and Written Opinion," for PCT Application No. PCT/US2021/054055 mailed Mar. 14, 2022 (21 pages).

"Invitation to Pay Additional Fees," for PCT Application No. PCT/US2021/054055 mailed Jan. 19, 2022 (16 pages).

"Response to Communication Pursuant to Rules 161(1) and 162 EPC," for European Patent Application No. 20757982.2 filed Aug. 16, 2022 (34 pages).

"Non-Final Office Action," for Japanese Patent Application No. 2021-571466 mailed Mar. 1, 2024 (7 pages).

"Non-Final Office Action," for U.S. Appl. No. 17/496,385 mailed Apr. 8, 2024 (56 pages).

"Non-Final Office Action," for U.S. Appl. No. 17/621,617 mailed Jan. 31, 2024 (28 pages).

"Response to Final Office Action," for U.S. Appl. No. 17/496,385, filed Mar. 13, 2024 (12 pages).

"Response to Non Final Office Action," for U.S. Appl. No. 17/621,617, filed Apr. 29, 2024 (10 pages).

"Second Office Action," for Chinese Patent Application No. 202080045491.5 mailed Mar. 2, 2024 (20 pages) with English Translation.

"International Preliminary Report on Patentability," for PCT Application No. PCT/US2021/054055 mailed Apr. 20, 2023 (15 pages).

"Aeration," Minnesota Rural Water Association, https://www.mrwa.com/WaterWorksMnl/Chapter%2011%20Aeration.pdf (Year: 2011), 8 pages.

"Cavitation," ScienceDirect, https://www.sciencedirect.com/topics/chemistry/cavitation (Year: 2019), 10 pages.

"Final Office Action," for Chinese Patent Application No. 202080045491.5 mailed Jul. 4, 2024 (27 pages) with English translation.

"Final Office Action," for U.S. Appl. No. 17/621,617 mailed Aug. 2, 2024 (27 pages).

"International Preliminary Report on Patentability," for PCT Patent Application No. PCT/US2023/015280 mailed Sep. 26, 2024 (9 pages).

"Notice of Allowance," for U.S. Appl. No. 17/496,385 mailed Sep. 28, 2024 (22 pages).

"Office Action," for Japanese Patent Application No. 2021-571466 mailed Oct. 4, 2024 (8 pages) with English translation.

"Response to Final Office Action," for U.S. Appl. No. 17/621,617, filed Nov. 1, 2024 (10 pages).

"Response to Non Final Office Action," for U.S. Appl. No. 17/496,385, filed Jun. 28, 2024 (19 pages).

"Vapor," Merriam Webster, https://www.merriam-webster.com/dictionary/vapor (Year: 2024), 13 pages.

"Notice of Allowance," for U.S. Appl. No. 17/621,617 mailed Apr. 11, 2025 (18 pages).

* cited by examiner

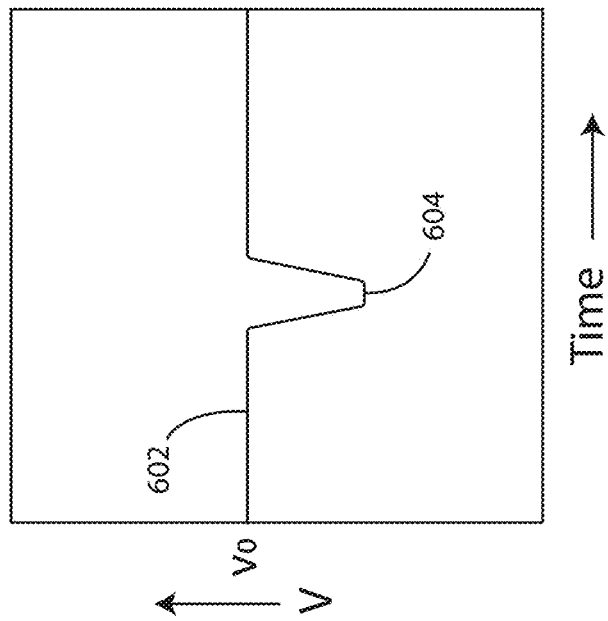
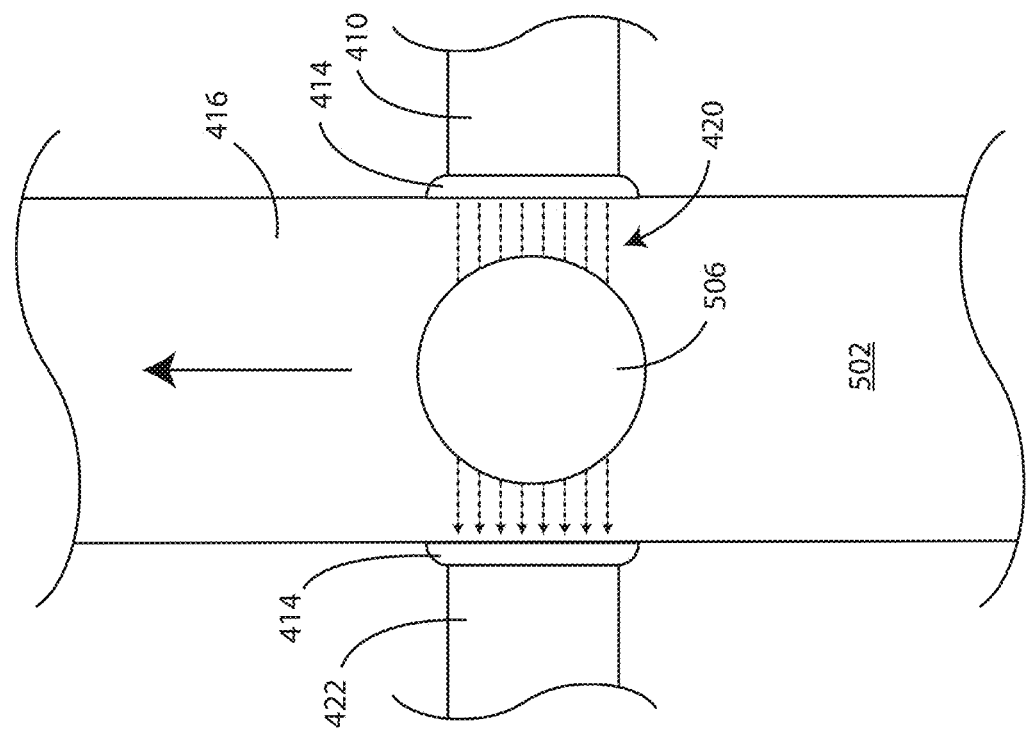

ant AIR BUBBLE SENSING SYSTEMS AND
RELATED SIGNAL PROCESSING

RELATED SIGNAL PROCESSING

This application claims the benefit of U.S. Provisional Application No. 63/320,557, filed Mar. 16, 2022, the content of which is herein incorporated by reference in its entirety.

FIELD

Embodiments herein relate to systems for detecting air bubbles in fluids and related systems and methods.

BACKGROUND

Air bubbles can be present in various fluids used with equipment such as fuel, hydraulic fluid, coolants, lubricants, and the like. The presence of air bubbles can have various causes including air leaks, contamination, cavitation, turbulent flow or mixing in a reservoir or tank, and the like. Unfortunately, air bubbles can cause various problems. By way of example, in a hydraulic system air bubbles can result in foaming of the fluid, erratic actuator movements, and banging or knocking noises. In a fuel system, air bubbles can cause an engine to run erratically or even cause damage.

SUMMARY

Embodiments herein relate to systems for detecting air bubbles in fluids and related systems and methods. In a first aspect, a fluid system aeration detector can be included having an optical air bubble sensor. The optical air bubble sensor can include a light source, a light detector, and a sensor controller. The sensor controller can be in signal communication with the light detector and can be configured to detect air bubbles based on the signals received from the light detector and estimate an amount of aeration of a fluid based on the detected air bubbles.

In a second aspect, in addition to one or more of the preceding or following aspects, or in the alternative to some aspects, the sensor controller can be configured to distinguish between air bubbles and water droplets in a fluid based on at least one of peak magnitude and peak width.

In a third aspect, in addition to one or more of the preceding or following aspects, or in the alternative to some aspects, the sensor controller can be configured to distinguish between air bubbles and water droplets based on a ratio of peak magnitude to peak width.

In a fourth aspect, in addition to one or more of the preceding or following aspects, or in the alternative to some aspects, the sensor controller can be configured to distinguish between air bubbles and water droplets based on peak magnitude.

In a fifth aspect, in addition to one or more of the preceding or following aspects, or in the alternative to some aspects, the sensor controller can be configured to distinguish between air bubbles and water droplets based on a magnitude of a reflection peak prior to a peak resulting from absorbance, refraction, and/or scattering.

In a sixth aspect, in addition to one or more of the preceding or following aspects, or in the alternative to some aspects, the fluid system aeration detector can be an on-vehicle sensing system.

In a seventh aspect, in addition to one or more of the preceding or following aspects, or in the alternative to some aspects, the optical air bubble sensor can be configured to be disposed downstream from a filter and upstream from a fluid pump.

In an eighth aspect, in addition to one or more of the preceding or following aspects, or in the alternative to some aspects, the optical air bubble sensor can be configured to be connected to a line for fluid flowing out of a fluid reservoir tank.

In a ninth aspect, in addition to one or more of the preceding or following aspects, or in the alternative to some aspects, the optical air bubble sensor can be configured to be connected to a kidney loop of a fluid reservoir tank.

In a tenth aspect, in addition to one or more of the preceding or following aspects, or in the alternative to some aspects, the optical air bubble sensor can be configured to be disposed within the fluid system at an area under vacuum pressure.

In an eleventh aspect, in addition to one or more of the preceding or following aspects, or in the alternative to some aspects, the optical air bubble sensor can further include a sampling channel, wherein the sampling channel can be in fluid communication with a fluid line of a vehicle.

In a twelfth aspect, in addition to one or more of the preceding or following aspects, or in the alternative to some aspects, the light source can be configured to emit light into the sampling channel.

In a thirteenth aspect, in addition to one or more of the preceding or following aspects, or in the alternative to some aspects, the light source can be configured to emit near-infrared light, ultraviolet, and/or visible spectrum light.

In a fourteenth aspect, in addition to one or more of the preceding or following aspects, or in the alternative to some aspects, the fluid system aeration detector can be configured to initiate generation of an alert if a count of detected air bubbles over a period of time exceeds a threshold value.

In a fifteenth aspect, in addition to one or more of the preceding or following aspects, or in the alternative to some aspects, the fluid system aeration detector can be configured to initiate generation of an alert if a detected volume of air bubbles exceeds a threshold value.

In a sixteenth aspect, in addition to one or more of the preceding or following aspects, or in the alternative to some aspects, the fluid system aeration detector can be configured to track a count, a size distribution, and/or a volume of detected air bubbles over time.

In a seventeenth aspect, a method of detecting fluid system aeration can be included herein. The method can include detecting air bubbles based on the signals received from a light detector and estimating an amount of aeration of a fluid based on the detected air bubbles.

In an eighteenth aspect, in addition to one or more of the preceding or following aspects, or in the alternative to some aspects, the method can further include distinguishing between air bubbles and water droplets in a fluid based on at least one of peak magnitude and peak width.

In a nineteenth aspect, in addition to one or more of the preceding or following aspects, or in the alternative to some aspects, the method can further include distinguishing between air bubbles and water droplets based on a ratio of peak magnitude to peak width.

In a twentieth aspect, in addition to one or more of the preceding or following aspects, or in the alternative to some aspects, the method can further include distinguishing between air bubbles and water droplets based on peak magnitude.

In a twenty-first aspect, in addition to one or more of the preceding or following aspects, or in the alternative to some aspects, the method can further include distinguishing between air bubbles and water droplets based on a magnitude of a reflection peak prior to a peak resulting from absorbance, refraction, and/or scattering.

In a twenty-second aspect, in addition to one or more of the preceding or following aspects, or in the alternative to some aspects, the light detector can be configured to be disposed downstream from a filter and upstream from a fluid pump.

In a twenty-third aspect, in addition to one or more of the preceding or following aspects, or in the alternative to some aspects, the light detector can be configured to be connected to a line for fluid flowing out of a fluid reservoir tank.

In a twenty-fourth aspect, in addition to one or more of the preceding or following aspects, or in the alternative to some aspects, the light detector can be configured to be connected to a kidney loop of a fluid reservoir tank.

In a twenty-fifth aspect, in addition to one or more of the preceding or following aspects, or in the alternative to some aspects, the light detector can be configured to be disposed within the fluid system at an area under vacuum pressure.

In a twenty-sixth aspect, in addition to one or more of the preceding or following aspects, or in the alternative to some aspects, the method can further include emitting light into a sampling channel.

In a twenty-seventh aspect, in addition to one or more of the preceding or following aspects, or in the alternative to some aspects, emitting light into a sampling channel includes emitting near-infrared light, ultraviolet, and/or visible spectrum light.

In a twenty-eighth aspect, in addition to one or more of the preceding or following aspects, or in the alternative to some aspects, the method can further include initiating generation of an alert if a count of detected air bubbles over a period of time exceeds a threshold value.

In a twenty-ninth aspect, in addition to one or more of the preceding or following aspects, or in the alternative to some aspects, the method can further include initiating generation of an alert if a detected volume of air bubbles exceeds a threshold value.

In a thirtieth aspect, in addition to one or more of the preceding or following aspects, or in the alternative to some aspects, the method can further include tracking a count, a size distribution, and/or a volume of detected air bubbles over time.

In a thirty-first aspect, a hydraulic system air bubble detector can be included having an optical air bubble sensor. The optical air bubble sensor can include a light source, a light detector, and a sensor controller. The sensor controller can be in signal communication with the light detector and can be configured to detect air bubbles based on the signals received from the light detector and estimate an amount of air in a hydraulic fluid line based on the detected air bubbles.

In a thirty-second aspect, in addition to one or more of the preceding or following aspects, or in the alternative to some aspects, the sensor controller can be configured to distinguish between air bubbles and water droplets in a fluid based on at least one of peak magnitude and peak width.

In a thirty-third aspect, in addition to one or more of the preceding or following aspects, or in the alternative to some aspects, the sensor controller can be configured to distinguish between air bubbles and water droplets based on a ratio of peak magnitude to peak width.

In a thirty-fourth aspect, in addition to one or more of the preceding or following aspects, or in the alternative to some aspects, the sensor controller can be configured to distinguish between air bubbles and water droplets based on peak magnitude.

In a thirty-fifth aspect, in addition to one or more of the preceding or following aspects, or in the alternative to some aspects, the sensor controller can be configured to distinguish between air bubbles and water droplets based on a magnitude of a reflection peak prior to a peak resulting from absorbance, refraction, and/or scattering.

In a thirty-sixth aspect, in addition to one or more of the preceding or following aspects, or in the alternative to some aspects, the hydraulic system air bubble detector can be an on-vehicle sensing system.

In a thirty-seventh aspect, in addition to one or more of the preceding or following aspects, or in the alternative to some aspects, the optical air bubble sensor can be configured to be disposed downstream from a filter and upstream from a fluid pump.

In a thirty-eighth aspect, in addition to one or more of the preceding or following aspects, or in the alternative to some aspects, the optical air bubble sensor can be configured to be connected to a return line back to a hydraulic fluid reservoir tank.

In a thirty-ninth aspect, in addition to one or more of the preceding or following aspects, or in the alternative to some aspects, the optical air bubble sensor can be configured to be connected to a line for fluid flowing out of a hydraulic fluid reservoir tank.

In a fortieth aspect, in addition to one or more of the preceding or following aspects, or in the alternative to some aspects, the optical air bubble sensor can be configured to be connected to a kidney loop of a hydraulic fluid reservoir tank.

In a forty-first aspect, in addition to one or more of the preceding or following aspects, or in the alternative to some aspects, the optical air bubble sensor can be configured to be disposed within a hydraulic fluid system at an area under vacuum pressure.

In a forty-second aspect, in addition to one or more of the preceding or following aspects, or in the alternative to some aspects, the optical air bubble sensor further can include a sampling channel, wherein the sampling channel can be in fluid communication with a hydraulic line of a vehicle.

In a forty-third aspect, in addition to one or more of the preceding or following aspects, or in the alternative to some aspects, the light source can be configured to emit light into the sampling channel.

In a forty-fourth aspect, in addition to one or more of the preceding or following aspects, or in the alternative to some aspects, the hydraulic system air bubble detector can be configured to initiate generation of an alert if a count of detected air bubbles over a period of time exceeds a threshold value.

In a forty-fifth aspect, in addition to one or more of the preceding or following aspects, or in the alternative to some aspects, the hydraulic system air bubble detector can be configured to initiate generation of an alert if a detected volume of air bubbles exceeds a threshold value.

In a forty-sixth aspect, in addition to one or more of the preceding or following aspects, or in the alternative to some aspects, the hydraulic system air bubble detector can be configured to track a count, a size distribution, and/or a volume of detected air bubbles over time.

In a forty-seventh aspect, in addition to one or more of the preceding or following aspects, or in the alternative to some aspects, the light source can be configured to emit near-infrared light, ultraviolet, and/or visible spectrum light.

In a forty-eighth aspect, a method of estimating an amount of air in a hydraulic fluid line can be included. The method can include detecting air bubbles based on the signals received from a light detector and estimating an amount of air in a hydraulic fluid line based on the detected air bubbles.

In a forty-ninth aspect, in addition to one or more of the preceding or following aspects, or in the alternative to some aspects, the method can further include distinguishing between air bubbles and water droplets in a fluid based on at least one of peak magnitude and peak width.

In a fiftieth aspect, in addition to one or more of the preceding or following aspects, or in the alternative to some aspects, the method can further include distinguishing between air bubbles and water droplets based on a ratio of peak magnitude to peak width.

In a fifty-first aspect, in addition to one or more of the preceding or following aspects, or in the alternative to some aspects, the method can further include distinguishing between air bubbles and water droplets based on peak magnitude.

In a fifty-second aspect, in addition to one or more of the preceding or following aspects, or in the alternative to some aspects, the method can further include distinguishing between air bubbles and water droplets based on a magnitude of a reflection peak prior to a peak resulting from absorbance, refraction, and/or scattering.

In a fifty-third aspect, in addition to one or more of the preceding or following aspects, or in the alternative to some aspects, the method can further include emitting light into a sampling channel.

In a fifty-fourth aspect, in addition to one or more of the preceding or following aspects, or in the alternative to some aspects, wherein emitting light into a sampling channel includes emitting near-infrared light, ultraviolet, and/or visible spectrum light.

In a fifty-fifth aspect, in addition to one or more of the preceding or following aspects, or in the alternative to some aspects, the method can further include initiating generation of an alert if a count of detected air bubbles over a period of time exceeds a threshold value.

In a fifty-sixth aspect, in addition to one or more of the preceding or following aspects, or in the alternative to some aspects, the method can further include initiating generation of an alert if a detected volume of air bubbles exceeds a threshold value.

In a fifty-seventh aspect, in addition to one or more of the preceding or following aspects, or in the alternative to some aspects, the method can further include tracking a count, a size distribution, and/or a volume of detected air bubbles over time.

In a fifty-eighth aspect, a pressure sensing system can be included having an optical air bubble sensor. The optical air bubble sensor can include a light source, a light detector, and a sensor controller. The sensor controller can be in signal communication with the light detector and can be configured to detect air bubbles based on the signals received from the light detector and estimate an amount of pressure in a fluid line based on the detected air bubbles.

In a fifty-ninth aspect, in addition to one or more of the preceding or following aspects, or in the alternative to some aspects, the sensor controller can be configured to distinguish between air bubbles and water droplets in a fluid based on at least one of peak magnitude and peak width.

In a sixtieth aspect, in addition to one or more of the preceding or following aspects, or in the alternative to some aspects, the sensor controller can be configured to distinguish between air bubbles and water droplets based on a ratio of peak magnitude to peak width.

In a sixty-first aspect, in addition to one or more of the preceding or following aspects, or in the alternative to some aspects, the sensor controller can be configured to distinguish between air bubbles and water droplets based on peak magnitude.

In a sixty-second aspect, in addition to one or more of the preceding or following aspects, or in the alternative to some aspects, the sensor controller can be configured to distinguish between air bubbles and water droplets based on a magnitude of a reflection peak prior to a peak resulting from absorbance, refraction, and/or scattering.

In a sixty-third aspect, in addition to one or more of the preceding or following aspects, or in the alternative to some aspects, the pressure sensing system can be an on-vehicle sensing system.

In a sixty-fourth aspect, in addition to one or more of the preceding or following aspects, or in the alternative to some aspects, the optical air bubble sensor can be configured to be disposed downstream from a filter and upstream from a fluid pump.

In a sixty-fifth aspect, in addition to one or more of the preceding or following aspects, or in the alternative to some aspects, further can include a sampling channel, wherein the sampling channel can be in fluid communication with a fluid line of a vehicle.

In a sixty-sixth aspect, in addition to one or more of the preceding or following aspects, or in the alternative to some aspects, the light source can be configured to emit light into the sampling channel.

In a sixty-seventh aspect, in addition to one or more of the preceding or following aspects, or in the alternative to some aspects, the pressure sensing system can be configured to initiate generation of an alert if a count over a period of time, a size distribution, and/or a volume of detected air bubbles crosses a threshold value.

In a sixty-eighth aspect, in addition to one or more of the preceding or following aspects, or in the alternative to some aspects, the pressure sensing system can be configured to track a count, a size distribution, and/or a volume of detected air bubbles over time.

In a sixty-ninth aspect, in addition to one or more of the preceding or following aspects, or in the alternative to some aspects, the light source can be configured to emit near-infrared light, ultraviolet, and/or visible spectrum light.

In a seventieth aspect, a method of estimating an amount of pressure in a fluid line can be included. The method can include detecting air bubbles based on the signals received from a light detector and estimating an amount of pressure in a fluid line based on the detected air bubbles.

In a seventy-first aspect, in addition to one or more of the preceding or following aspects, or in the alternative to some aspects, the method can further include distinguishing between air bubbles and water droplets in a fluid based on at least one of peak magnitude and peak width.

In a seventy-second aspect, in addition to one or more of the preceding or following aspects, or in the alternative to some aspects, the method can further include distinguishing between air bubbles and water droplets based on a ratio of peak magnitude to peak width.

In a seventy-third aspect, in addition to one or more of the preceding or following aspects, or in the alternative to some aspects, the method can further include distinguishing between air bubbles and water droplets based on peak magnitude.

In a seventy-fourth aspect, in addition to one or more of the preceding or following aspects, or in the alternative to some aspects, the method can further include distinguishing between air bubbles and water droplets based on a magnitude of a reflection peak prior to a peak resulting from absorbance, refraction, and/or scattering.

In a seventy-fifth aspect, in addition to one or more of the preceding or following aspects, or in the alternative to some aspects, the method can further include emitting light into a sampling channel.

In a seventy-sixth aspect, in addition to one or more of the preceding or following aspects, or in the alternative to some aspects, wherein emitting light into a sampling channel includes emitting near-infrared light, ultraviolet, and/or visible spectrum light.

In a seventy-seventh aspect, in addition to one or more of the preceding or following aspects, or in the alternative to some aspects, the method can further include initiating generation of an alert if a count of detected air bubbles over a period of time exceeds a threshold value.

In a seventy-eighth aspect, in addition to one or more of the preceding or following aspects, or in the alternative to some aspects, the method can further include tracking a count, a size distribution, and/or a volume of detected air bubbles over time.

In a seventy-ninth aspect, a filter restriction sensing system can be included having an optical air bubble sensor. The optical air bubble sensor can include a light source, a light detector, and a sensor controller. The sensor controller can be in signal communication with the light detector and can be configured to evaluate signals received from the light detector, detect air bubbles based on the signals received from the light detector, and generate an estimate of a restriction level of a liquid filter upstream from the light detector based on the detected air bubbles.

In an eightieth aspect, in addition to one or more of the preceding or following aspects, or in the alternative to some aspects, the optical air bubble sensor can be configured to be disposed within a fuel system at an area under vacuum pressure.

In an eighty-first aspect, in addition to one or more of the preceding or following aspects, or in the alternative to some aspects, the optical air bubble sensor can be configured to be disposed within a fuel system of a vehicle at an area under vacuum pressure.

In an eighty-second aspect, in addition to one or more of the preceding or following aspects, or in the alternative to some aspects, the optical air bubble sensor can be configured to be disposed within a hydraulic system at an area under vacuum pressure.

In an eighty-third aspect, in addition to one or more of the preceding or following aspects, or in the alternative to some aspects, the optical air bubble sensor can be configured to be disposed downstream from a filter and upstream from a fluid pump.

In an eighty-fourth aspect, in addition to one or more of the preceding or following aspects, or in the alternative to some aspects, the optical air bubble sensor can be configured to be disposed downstream from a filter and upstream from a hydraulic fluid pump.

In an eighty-fifth aspect, in addition to one or more of the preceding or following aspects, or in the alternative to some aspects, the sensor controller can be configured to distinguish between air bubbles and water droplets in a fluid based on at least one of peak magnitude and peak width.

In an eighty-sixth aspect, in addition to one or more of the preceding or following aspects, or in the alternative to some aspects, the sensor controller can be configured to distinguish between air bubbles and water droplets based on a ratio of peak magnitude to peak width.

In an eighty-seventh aspect, in addition to one or more of the preceding or following aspects, or in the alternative to some aspects, the sensor controller can be configured to distinguish between air bubbles and water droplets based on peak magnitude.

In an eighty-eighth aspect, in addition to one or more of the preceding or following aspects, or in the alternative to some aspects, the sensor controller can be configured to distinguish between air bubbles and water droplets based on a magnitude of a reflection peak prior to a peak resulting from absorbance, refraction, and/or scattering.

In an eighty-ninth aspect, in addition to one or more of the preceding or following aspects, or in the alternative to some aspects, the filter restriction sensing system can be an on-vehicle sensing system.

In a ninetieth aspect, in addition to one or more of the preceding or following aspects, or in the alternative to some aspects, the filter restriction sensing system can be fuel filter restriction sensing system.

In a ninety-first aspect, in addition to one or more of the preceding or following aspects, or in the alternative to some aspects, the filter restriction sensing system can be hydraulic fluid filter restriction sensing system.

In a ninety-second aspect, in addition to one or more of the preceding or following aspects, or in the alternative to some aspects, the filter restriction sensing system can further include a sampling channel, wherein the sampling channel can be in fluid communication with a fluid line of a vehicle.

In a ninety-third aspect, in addition to one or more of the preceding or following aspects, or in the alternative to some aspects, the light source can be configured to emit light into the sampling channel.

In a ninety-fourth aspect, in addition to one or more of the preceding or following aspects, or in the alternative to some aspects, the light source can be configured to emit near-infrared light, ultraviolet, and/or visible spectrum light.

In a ninety-fifth aspect, in addition to one or more of the preceding or following aspects, or in the alternative to some aspects, an inlet to the sampling channel can be located along a curved portion of a fluid flow channel.

In a ninety-sixth aspect, in addition to one or more of the preceding or following aspects, or in the alternative to some aspects, an inlet to the sampling channel faces at least partially upward with respect to the direction of gravity.

In a ninety-seventh aspect, in addition to one or more of the preceding or following aspects, or in the alternative to some aspects, the filter restriction sensing system can be configured to generate an estimate of a restriction level of a fluid filter upstream from the light detector based on one or more properties of detected air bubbles.

In a ninety-eighth aspect, in addition to one or more of the preceding or following aspects, or in the alternative to some aspects, the properties of detected air bubbles can include at least one selected from the group consisting of average air bubble size, maximum air bubble size, counts of air bubbles, and air bubble volume as a percentage of total fluid volume.

In a ninety-ninth aspect, in addition to one or more of the preceding or following aspects, or in the alternative to some aspects, the filter restriction sensing system can be further configured to generate the estimate of a restriction level using a fluid flow rate through the filter.

In a one hundred and aspect, in addition to one or more of the preceding or following aspects, or in the alternative to some aspects, the filter restriction sensing system can be configured to determine an end of life of the fluid filter based on the estimated restriction level of the fluid filter.

In a one hundred and first aspect, in addition to one or more of the preceding or following aspects, or in the alternative to some aspects, the filter restriction sensing system can be configured to initiate generation of an alert if a count over a period of time, a size distribution, and/or a volume of detected air bubbles crosses a threshold value.

In a one hundred and second aspect, in addition to one or more of the preceding or following aspects, or in the alternative to some aspects, the filter restriction sensing system can be configured to track a count, a size distribution, and/or a volume of detected air bubbles over time.

In a one hundred and third aspect, a method of determining a level of restriction of a filter can be included, the method including evaluating signals received from a light detector, detecting air bubbles based on the signals received from the light detector, and generating an estimate of a restriction level of a liquid filter upstream from the light detector based on the detected air bubbles.

In a one hundred and fourth aspect, in addition to one or more of the preceding or following aspects, or in the alternative to some aspects, the light detector can be disposed within a fuel system at an area under vacuum pressure.

In a one hundred and fifth aspect, in addition to one or more of the preceding or following aspects, or in the alternative to some aspects, the light detector can be disposed within a hydraulic system at an area under vacuum pressure.

In a one hundred and sixth aspect, in addition to one or more of the preceding or following aspects, or in the alternative to some aspects, the light detector can be disposed within a hydraulic system downstream from the filter and upstream from a fluid pump.

In a one hundred and seventh aspect, in addition to one or more of the preceding or following aspects, or in the alternative to some aspects, the light detector can be disposed within a hydraulic system downstream from the filter and upstream from a hydraulic fluid pump.

In a one hundred and eighth aspect, in addition to one or more of the preceding or following aspects, or in the alternative to some aspects, the method can further include distinguishing between air bubbles and water droplets in a fluid based on at least one of peak magnitude and peak width.

In a one hundred and ninth aspect, in addition to one or more of the preceding or following aspects, or in the alternative to some aspects, the method can further include distinguishing between air bubbles and water droplets based on a ratio of peak magnitude to peak width.

In a one hundred and tenth aspect, in addition to one or more of the preceding or following aspects, or in the alternative to some aspects, the method can further include distinguishing between air bubbles and water droplets based on peak magnitude.

In a one hundred and eleventh aspect, in addition to one or more of the preceding or following aspects, or in the alternative to some aspects, the method can further include distinguishing between air bubbles and water droplets based on a magnitude of a reflection peak prior to a peak resulting from absorbance, refraction, and/or scattering.

In a one hundred and twelfth aspect, in addition to one or more of the preceding or following aspects, or in the alternative to some aspects, the method can further include emitting light into a sampling channel.

In a one hundred and thirteenth aspect, in addition to one or more of the preceding or following aspects, or in the alternative to some aspects, emitting light into a sampling channel includes emitting near-infrared light, ultraviolet, and/or visible spectrum light.

In a one hundred and fourteenth aspect, in addition to one or more of the preceding or following aspects, or in the alternative to some aspects, the method can further include generating an estimate of a restriction level of a fluid filter upstream from the light detector based on one or more properties of detected air bubbles.

In a one hundred and fifteenth aspect, in addition to one or more of the preceding or following aspects, or in the alternative to some aspects, generating an estimate of a restriction level of a fluid filter upstream from the light detector based on one or more the properties of detected air bubbles includes generating the estimate of a restriction level using a fluid flow rate through the filter.

In a one hundred and sixteenth aspect, in addition to one or more of the preceding or following aspects, or in the alternative to some aspects, the method can further include determining an end of life of the fluid filter based on the estimated restriction level of the fluid filter.

In a one hundred and seventeenth aspect, in addition to one or more of the preceding or following aspects, or in the alternative to some aspects, the method can further include initiating generation of an alert if a count of detected air bubbles over a period of time exceeds a threshold value.

In a one hundred and eighteenth aspect, in addition to one or more of the preceding or following aspects, or in the alternative to some aspects, the method can further include tracking a count, a size distribution, and/or a volume of detected air bubbles over time.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 5 is a schematic view of a portion of an air bubble sensing system in accordance with various embodiments herein.

FIG. 6 is a view of potential versus time for a sensing system in accordance with various embodiments herein.

Figure 1:
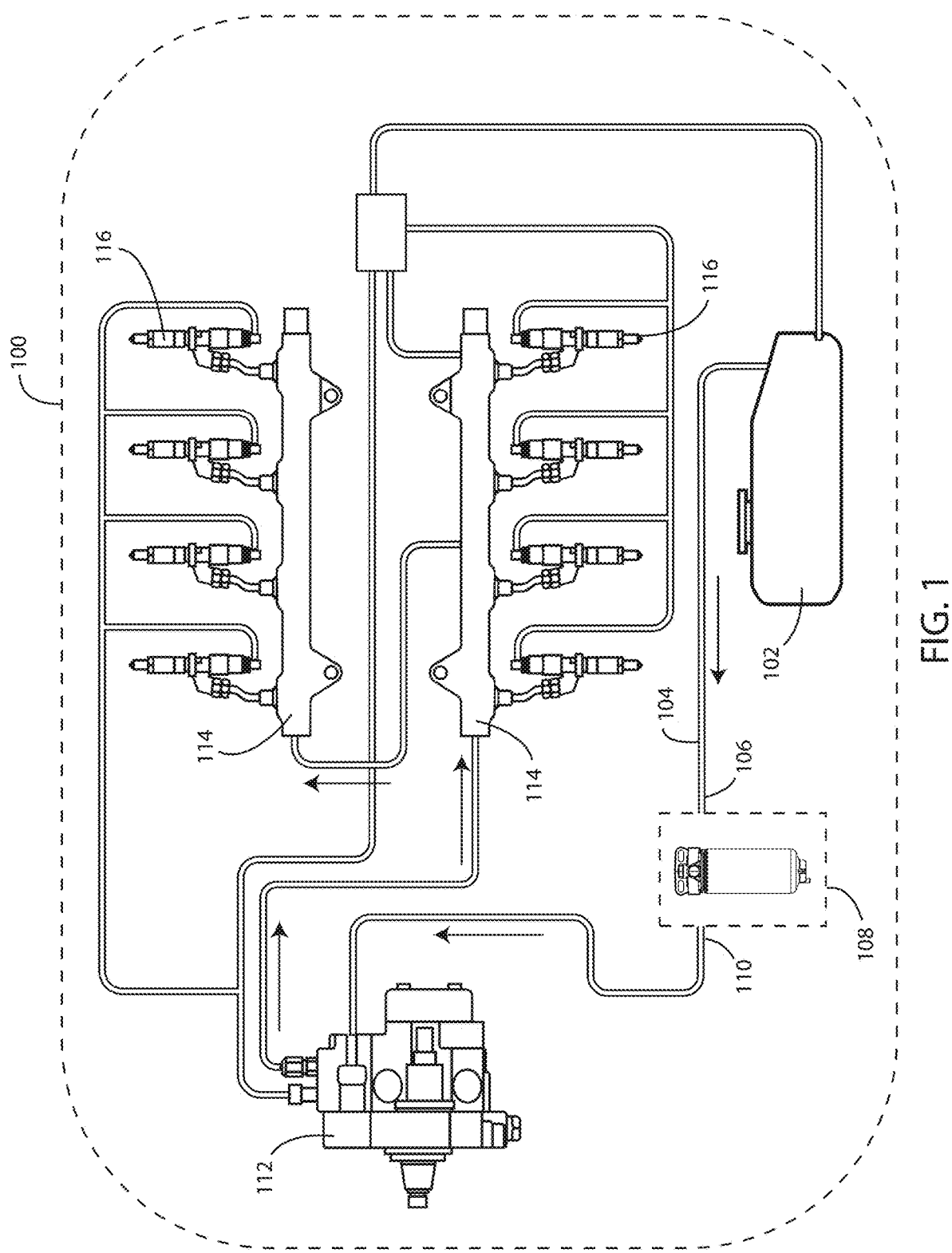
FIG. 1 is a schematic view of a fuel system in accordance with various embodiments herein.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As discussed above, air bubbles in fluid can cause various problems. Therefore, it can be desirable to detect and/or track the presence of air bubbles in a system. Further, the presence of air bubbles can provide insight into possible problems with the system such as an air leak or the need for a filter system to be serviced. In some cases, the presence of air bubbles can also be used as a proxy for detecting pressure as the presence of air bubbles can be related to pressure (such as how air bubbles can form from dissolved air when the fluid is under vacuum pressure). Further, pressure can be correlated with a degree of filter restriction.

Embodiments herein can include fluid system aeration detectors including an optical air bubble sensor. The optical air bubble sensor can include a light source, a light detector, and a sensor controller. The sensor controller can be in signal communication with the light detector. The sensor controller can be configured to detect air bubbles based on the signals received from the light detector and estimate an amount of aeration of a fluid based on the detected air bubbles.

Embodiments herein can include air bubble sensing systems that can detect the presence of air bubbles in a fluid. In some embodiments, the sensing systems can specifically be on-vehicle. By being on-vehicle, the system can provide information that may be useful to a vehicle operator, fleet controller, or the like to support operation of the vehicle while mitigating potential damage. For example, the amount of air bubbles in fluid for a vehicle can result in recommendations being made by the system related to servicing of the vehicle including servicing frequency, the type of fluid filter being used, and the like. In some scenarios, if the amount of air bubbles in fluid rises above a threshold level, then a recommendation can be made to discontinue operation of the vehicle until maintenance services can be performed.

Embodiments herein can also include a hydraulic system air bubble detector. The air bubble detector can include an optical air bubble sensor. The optical air bubble sensor can include a light source, a light detector, and a sensor controller. The sensor controller can be in signal communication with the light detector. The sensor controller can be configured to detect air bubbles based on the signals received from the light detector and estimate an amount of air in a hydraulic fluid line based on the detected air bubbles.

Embodiments herein can also include a pressure sensing system including an optical air bubble sensor. Pressure can influence air bubbles (all things equal lower pressures result in a greater volume of air bubbles) and therefore information regarding air bubbles can be used to sense pressure. The optical air bubble sensor can include a light source, a light detector, and a sensor controller. The sensor controller can be in signal communication with the light detector and can be configured to detect air bubbles based on the signals received from the light detector and estimate an amount of pressure in a fluid line based on the detected air bubbles.

Embodiments herein can also include a filter restriction sensing system including an optical air bubble sensor. Filter restriction can be reflected in pressure drop across the filter impacting pressures upstream and downstream of the filter. Pressure can influence air bubbles (all things equal lower pressures result in a greater volume of air bubbles) and therefore information regarding air bubbles can be used to sense filter restriction. The optical air bubble sensor can include a light source, a light detector, and a sensor controller. The sensor controller can be in signal communication with the light detector. The sensor controller can be configured to evaluate signals received from the light detector, detect air bubbles based on the signals received from the light detector, and generate an estimate of a restriction level of a liquid filter in fluid communication with (upstream from, downstream from, with or without other components—such as a pump—in between or on the other side of, etc.) the light detector based on the detected air bubbles.

In various embodiments, an air bubble sensing system herein can include a light source, a light detector, and a sensor controller. The sensor controller can be in signal communication with the light detector. The sensor controller can be configured to evaluate signals received from the light detector, identify air bubbles based on the signals received from the light detector, record information regarding the identified air bubbles, and generate an estimate of the amount of air or air bubbles in a fluid.

In various embodiments herein, an air bubble sensing system can distinguish between air bubbles and water droplets to allow for more accurate measurements of air bubbles. In various embodiments, the sensor controller can be configured to evaluate signals received from the light detector, distinguish between air bubbles and water droplets based on the signals received from the light detector, record information regarding the air bubbles; and generate an estimate of an amount of air or air bubbles in a fluid.

Air bubbles can occur within many different systems of a machine or vehicle. For example, air bubbles can occur within a fuel system. Referring now to FIG. 1, a schematic view of a fuel system 100 is shown in accordance with various embodiments herein. The fuel system 100 can include various components such as a fuel tank 102, a fuel line 104, and a fuel filter system 108. The fuel system 100 can also include a fuel pump 112, a fuel rail 114, and a plurality of fuel injectors 116. The fuel line 104 includes an upstream side 106 (e.g., upstream from the fuel filter system 108) and a downstream 110 side.

An air bubble sensing system herein can be mounted at various points along the fuel system 100. In some embodiments, the air bubble sensing system (or components thereof) can be mounted along a fuel line 104. In various embodiments, the air bubble sensing system can be mounted upstream 106 from a fuel filter. In various embodiments, the air bubble sensing system can be mounted downstream 110 from a fuel filter. In various embodiments, the air bubble sensing system can be mounted on or in a fuel filter head (described further below).

In some embodiments, the system can also be configured to receive information regarding a fuel level within the fuel tank 102. For example, in some embodiments, the system can cross-reference the fuel level information against recorded information regarding detected air bubbles. In some cases, the system can get the fuel level data directly from a sensor that is associated with the fuel tank. In some embodiments, the system can get the fuel level data from a vehicle data network, such as CANBus. "CANBus" refers to a vehicle data bus standard designed to allow devices and electronic control units to communicate with one another. Many vehicles include a CANBus network and communication with the CANBus network can provide many different types of data. For example, interfacing with the CANBus network can provide one or more of fuel level data, engine RPM data, engine hours of operation data, odometer data, engine/vehicle temperature data, fuel consumption data, fuel system data, ambient temperature data, geolocation and/or altitude data, fuel flowrate and the like.

It will be appreciated that the fuel system shown in FIG. 1 is merely one example of a fuel system for which air bubble detection systems herein can work and the range of compatible fuel systems contemplated herein can include many different variations. By way of example, some fuel systems can include a two-filter system with a lift/transfer pump disposed in between. Thus, the fuel filter system 108 of FIG. 1 may reflect two filters with a lift/transfer pump in between. In such a system, the air bubble sensing system can be configured to detect air bubbles downstream from first filter, but upstream from the lift/transfer pump and second filter (e.g., an area with vacuum pressure). However, the air bubble sensing system can also detect air bubbles at other locations. In addition, embodiments of air bubble sensing systems for use with fuel systems herein may include those operative with fuel systems having any number of fuel filters.

Figure 2:
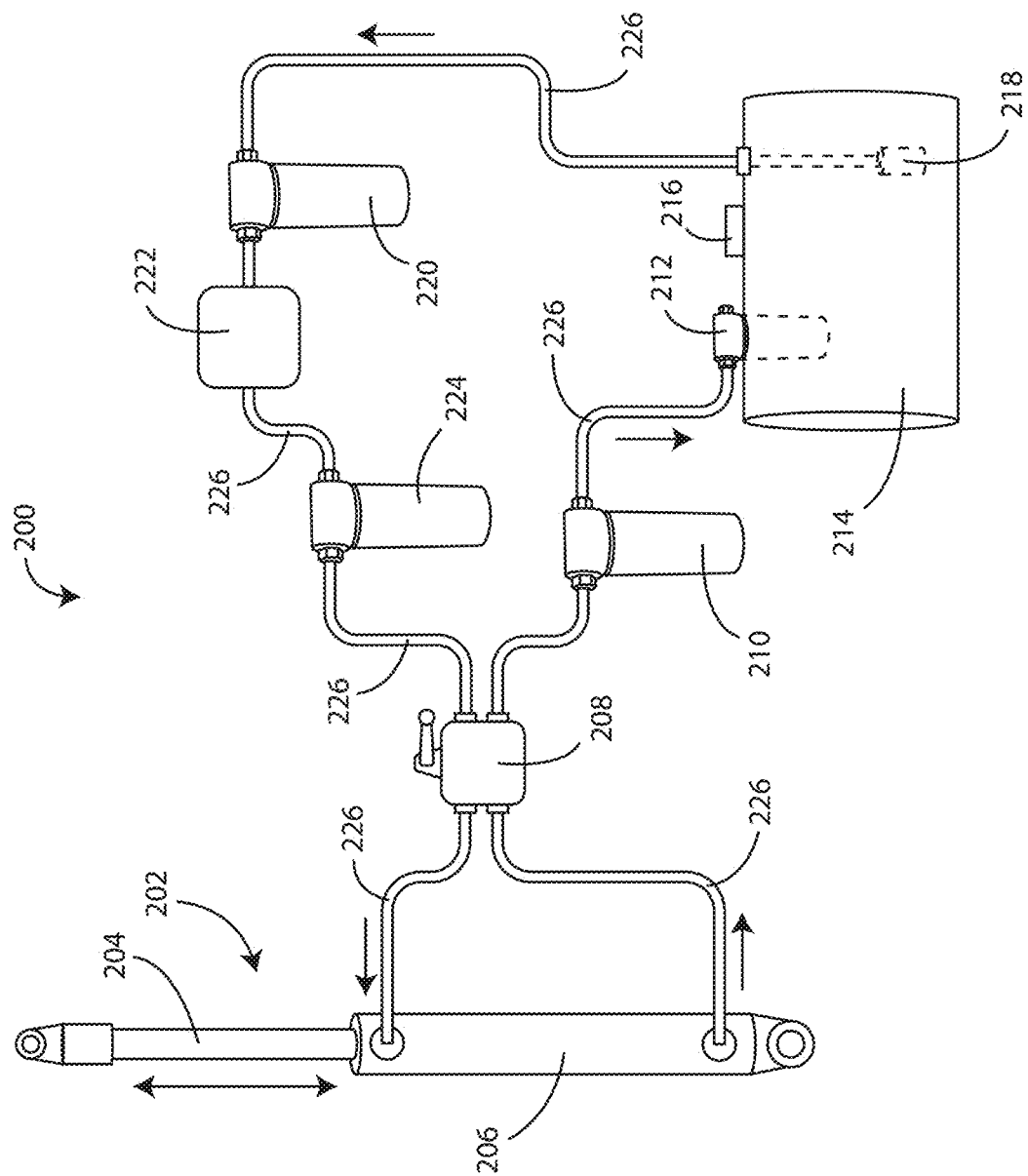
FIG. 2 is a schematic view of a hydraulic system in accordance with various embodiments herein.

Air bubbles can also occur within other types of systems with fluid lines such as a hydraulic system. Referring now to FIG. 2, a schematic view of a hydraulic system 200 is shown in accordance with various embodiments herein. It will be appreciated that in many embodiments of hydraulic systems not all of the various filters depicted in FIG. 2 may actually be present. The system 200 includes a hydraulic cylinder 202. The hydraulic cylinder 202 includes a cylinder barrel 206 and a piston rod 204. Hydraulic fluid moves through the system 200 as controlled with a control unit 208 and passes through a hydraulic fluid line 226. An amount of hydraulic fluid is stored within a reservoir tank 214 and passes through a strainer 218 before traveling through the hydraulic fluid line 226 and passing to a low (or suction) pressure filter 220 before going to a hydraulic fluid pump 222. The hydraulic fluid is then pumped to a medium or high-pressure filter 224 and then passes through the control unit 208 and then onto the hydraulic cylinder 202. On the return path, the hydraulic fluid then passes through the control unit 208 and then passes through a return line filter 210 before passing through an in-tank return filter 212 and entering the reservoir tank 214. The reservoir tank 214 can include a breather 216. In some embodiments, the hydraulic system 200 can also include a kidney loop system (not shown in this view). A kidney loop system can include a pump and a filter and can operate to pump fluid from the reservoir tank 214 through the filter and back to the reservoir tank 214 so that the kidney loop functions to clean the fluid within the reservoir tank 214.

An air bubble sensing system herein can be mounted at various points along the hydraulic system 200. In some embodiments, the air bubble sensing system (or components thereof) can be mounted along the hydraulic fluid line 226. In various embodiments, the air bubble sensing system can be mounted within or on a hydraulic system at an area under vacuum pressure. In various embodiments, the air bubble sensing system can be mounted within or on a hydraulic system downstream from a filter and upstream from a fluid pump. In various embodiments, the air bubble sensing system can be mounted downstream from a filter (such as any of the filters within a hydraulic system or specifically a low or suction pressure filter 220) and upstream from a hydraulic fluid pump. It will be appreciated, however, that air bubble sensing systems herein (or components of the same) can be mounted upstream or downstream of any of the fluid filters described herein or at other locations. In various embodiments, the air bubble sensing system can be mounted on or in a filter head.

Figure 3:
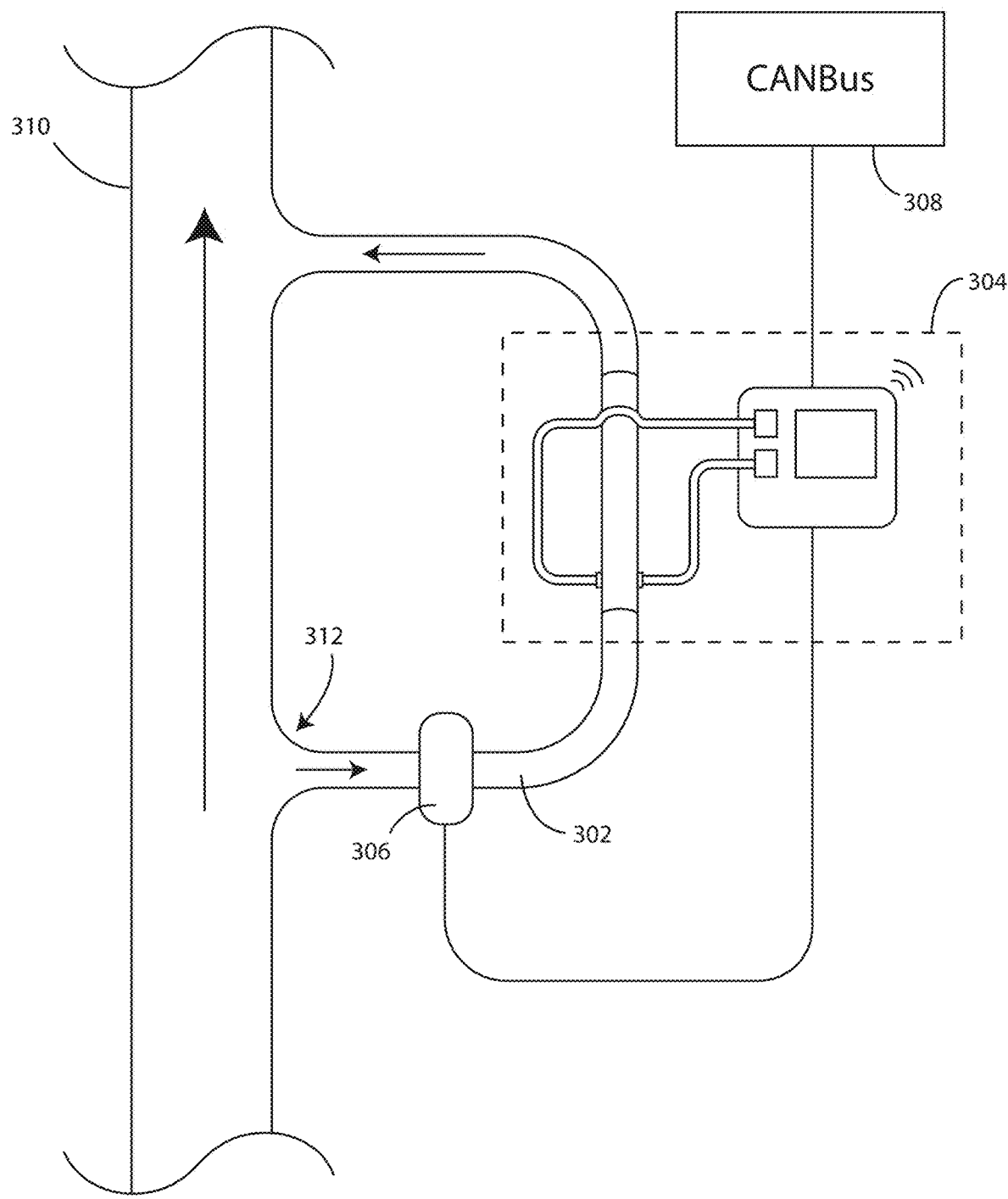
FIG. 3 is a schematic view of an air bubble sensing system in accordance with various embodiments herein.

Referring now to FIG. 3, a schematic view of an air bubble sensing system 304 is shown in accordance with various embodiments herein. As noted before, the air bubble sensing system 304 can be configured to be mounted on a vehicle in some embodiments. However, in other embodiments it can be mounted on a stationary piece of equipment such as a generator. FIG. 3 shows a fluid line 310 of the vehicle. FIG. 3 shows an air bubble sensing system 304. The air bubble sensing system 304 includes a flow channel 302. The flow channel 302 can be in fluid communication with the fluid line 310 of a vehicle or other piece of equipment. The flow channel 302 is typically a known fraction of the diameter and/or cross-sectional area of the fluid line 310 (e.g., 1:1, 1:5, 1:10, 1:25, 1:50, 1:100, 1:200, 1:500, 1:1000 or less, or within a range between any of those). Thus, a portion of the fluid that is flowing through the fluid line 310 can enter the flow channel 302 for testing by the air bubble sensing system 304.

In various embodiments herein, data regarding a flow rate can be used in combination with data regarding the number of air bubbles detected and the size of the water droplets detected to estimate the total amount of air bubbles in the fluid. It will be appreciated that there are at least two potentially different fluid flow rates to consider in making such a calculation. The first is the system fluid flow rate. The second is the sensor fluid flow rate, which is the flow rate of fluid through the flow channel 302 of the air bubble sensing system 304 described in FIG. 3. The system fluid flow rate can vary based on various factors including the operating state and/or load of the system. The sensor flowrate is typically much lower than the system fluid flow rate. The sensor flow rate can be from 0.2 mlpm (milliliters per minute) to 10 mlpm, 0.2 mlpm (milliliters per minute) to 5 mlpm, 0.2 mlpm (milliliters per minute) to 2 mlpm, or from 0.8 mlpm to 1.2 mlpm in some embodiments. The sensor flowrate is related to the system flow rate so as the system flow rate changes the sensor flow rate will also change. Converting from one flow rate to the other can be a matter of applying a simple calibration or relationship equation.

In some embodiments, the system can store data in a lookup table or similar data structure that relates the sensor flow rate and the system flow rate at various values for each and then converting between the two can simply be a matter of referencing the lookup table. In some embodiments, data relating the sensor flow rate and the system flow rate can be determined empirically.

In some embodiments, the air bubble sensing system 304 also includes a flow rate sensor 306. Data from the flow rate sensor 306 can be used, in combination with data regarding the number of air bubbles detected and the size of the air bubbles detected in order to estimate the total amount of air or air bubbles in the fluid. In some embodiments, the flow rate sensor 306 can be positioned so that it is detecting the sensor flow rate. In calculating/estimating the total amount of air bubbles in the fluid, the sensor flow rate can be determined and then this information can be used in combination with data regarding the number of air bubbles detected and the size of the air bubbles detected in order to estimate the total amount of air bubbles in the fluid. However, in some cases, a flow rate sensor may be positioned along a fluid line such that the flow rate obtained is the system fluid flow rate. In such cases, the system fluid flow rate can be converted to a sensor flow rate as discussed above.

In some embodiments, data regarding system fluid flow rates can be obtained in other ways and thus a flow rate sensor 306 may be omitted. For example, in some embodiments differential pressure (dP) can be used to calculate/estimate flow rate. The flow rate estimated in this manner can be either the system flow rate or the sensor flow rate. The system can include a differential pressure sensor and then calculate flow rate based on the relationship between dP and flow rate along using an assumption of laminar flow (within the sensor channel) and knowledge of fluid properties. In some embodiments, turbulent flow models can also be used as part of a flow rate calculation when evaluating flow rate (system flow rate) of the main flow channel. As another example, in some embodiments, the air bubble sensing system 304 can get information regarding fluid flow rates (or a piece of information from which fluid flow rates can be derived or otherwise estimated) from a vehicular data network 308. In some embodiments, the vehicular data network 308 can be a CANBUS network. But, in other embodiments the vehicular data network 308 can be another type of network that is wired or wireless. In various embodiments, the air bubble sensing system 304 can be configured to send information regarding the identified air bubbles to a vehicular data network 308.

In some embodiments, the components of the air bubble sensing system can be disposed such that buoyancy of the air bubbles promotes their entry into the inlet 312. This can lead to an increased amount of air bubbles entering the inlet 312. For example, in some embodiments an inlet 312 to the sampling channel is located along a curved portion of a fluid flow channel. In some embodiments, an inlet 312 to the sampling channel faces at least partially upward with respect the direction of gravity. In some embodiments, plumbing features can be included to achieve isokinetic sampling.

Figure 4:
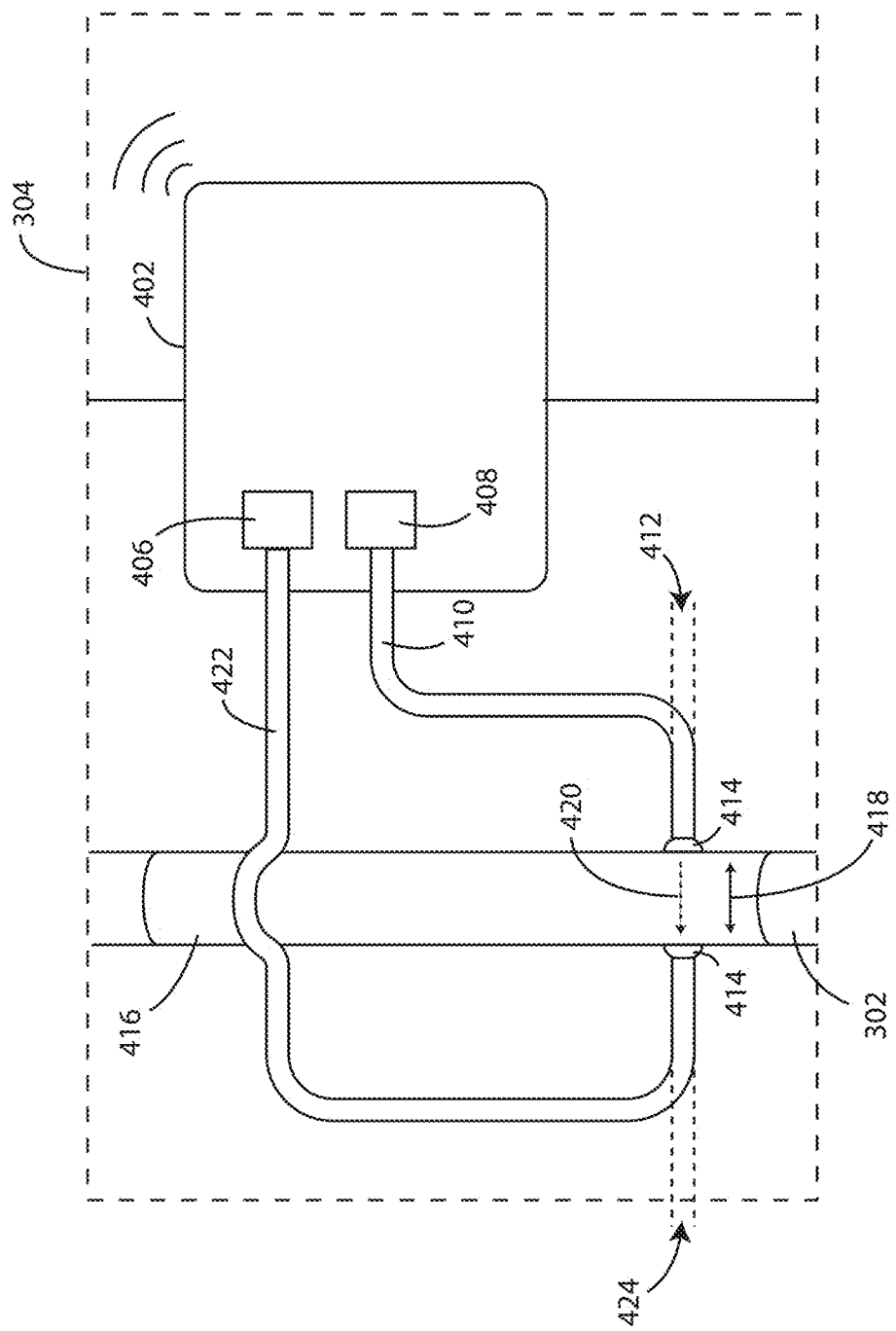
FIG. 4 is a schematic view of a portion of the air bubble sensing system of FIG. 3.

Referring now to FIG. 4, a schematic view is shown of a portion of the air bubble sensing system of FIG. 3. FIG. 4 shows an air bubble sensing system 304 including a flow channel 302. A fluid can flow from a fuel line, a hydraulic fluid line, a lubricant line, a coolant line, or the like (or a component connected to any of these) of a system or vehicle and into the flow channel. In some embodiments, the air bubble sensing system 304 also includes a flow cell 416. The flow cell 416 can be transparent, partially transparent, or at least include transparent portions and can be formed of various materials such as a glass or a polymer. The flow cell 416 (or another vessel with provisional for optical transmission) can be connected to the flow channel 302. Thus, a fluid can pass through the flow channel 302.

The air bubble sensing system 304 includes a light source 408. The air bubble sensing system 304 also includes a source light guide 410. In some embodiments, the air bubble sensing system 304 also includes an optical interface 414 providing an optical connection between the source light guide 410 and the flow cell 416. In this manner, a light emission 420 generated by the light source 408 can pass through the fluid in the flow cell 416.

A second optical interface 414 can provide an optical connection between the flow cell 416 and a detector light guide 422. The air bubble sensing system 304 also includes a light detector 406 that in optical communication with the detector light guide 422. In some embodiments, the light source 408, the light detector 406, and various other components can be disposed within a housing 402.

In some embodiments, the light source 408 can be a LED or other light emitter. In some embodiment, the light detector 406 can be a photodiode, phototransistor, photoresistor, CMOS sensor, a charge-coupled device, or the like. The source light guide 410 can be an optical fiber, a light pipe, or other structure capable of conveying an optical signal. Similarly, the detector light guide 422 can be an optical fiber, a light pipe, other structure capable of conveying an optical signal.

In operation, the light source can be configured to emit light into a sample of fluid (directly or indirectly) and the light detector can be configured to receive light that has passed through the sample (directly or indirectly). In the example of FIG. 4, the light source and light detector can be arranged to be in optical communication with components on opposing sides of the flow cell 416. The absorbance of air at certain wavelengths of light (including, but not limited to, ultraviolet wavelengths) is different than that of certain fluids such as hydrocarbon fluids (e.g., hydrocarbon fluids will absorb UV wavelength light whereas air will not) allowing for the detection of air bubbles through evaluation of absorbance at ultraviolet wavelengths. However, other wavelengths of light can also be used herein for the detection of air bubbles. For example, in some embodiments a wavelength of light can be used that is absorbed by $CO_2$ (or another component within air) differently than by the fluid containing the air bubbles. Further, other principles for the detection of air bubbles can also be applied other than absorbance. For example, the refractive index of air and certain fluids (such as fuel or hydrocarbon fluids) is different. This causes light to bend at any curved interface leading to an effect detectable with the light detector that is similar to the appearance of absorbance (e.g., light is bent away from the light detector). In such a case, light at many different wavelengths or bands can be used including, for example, light centered on 1550 nm or within other bands. Therefore, whether based on absorbance or another effect such as refraction, scattering, or the like, a signal from the light detector will vary based upon the amount of air bubbles in the fluid. The signal from the light detector can then be evaluated to determine the amount of air bubbles in the fluid passing through the sensor channel.

The flow channel 302 includes a channel diameter 418. The channel diameter 418 can have a diameter of various dimensions. In some embodiments, the diameter can be greater than or equal to 100 μm, 130 μm, 160 μm, 190 μm, 220 µm, or 250 µm. In some embodiments, the diameter can be less than or equal to 1000 µm, 850 µm, 700 µm, 550 µm, 400 µm, or 250 µm. In some embodiments, the diameter can fall within a range of 100 µm to 1000 µm, or 130 µm to 850 µm, or 160 µm to 700 µm, or 190 µm to 550 µm, or 220 µm to 400 µm.

The source light guide 410 can have a particular diameter 412. In some embodiments, the diameter 412 can be greater than or equal to 100 µm, 200 µm, 250 µm, 300 µm, 350 µm, or 400 µm. In some embodiments, the diameter 412 can be less than or equal to 800 µm, 700 µm, 600 µm, 500 µm, or 400 µm. In some embodiments, the diameter 412 can fall within a range of 100 µm to 800 µm, or 150 µm to 500 µm, or 200 µm to 300 µm, or 250 µm to 350 µm, or can be about 300 µm.

The detector light guide 422 can have a particular diameter 424. In some embodiments, the diameter 424 of the detector light guide 422 is less than the diameter 412 of the source light guide 410. In some embodiments, the diameter 424 can be greater than or equal to 100 µm, 125 µm, 150 µm, 175 µm, or 200 µm. In some embodiments, the diameter 424 can be less than or equal to 400 µm, 350 µm, 300 µm, 250 µm, or 200 µm. In some embodiments, the diameter 424 can fall within a range of 100 µm to 400 µm, or 125 µm to 350 µm, or 150 µm to 300 µm, or 175 µm to 250 µm, or can be about 200 µm. The light guide 422 can include, for example, light pipes, fiber optic components, liquid light guides, orifices, and the like.

Referring now to FIG. 5, a schematic view of a portion of an air bubble sensing system is shown in accordance with various embodiments herein. Fluid moves through a flow path 502 defined by the flow cell 416. A light emission 420 from a light source (not shown in this view) passes from the source light guide 410 to the optical interface 414, and then across the flow path 502 wherein it can encounter an air bubble 506. The light emission (as altered by its interactions with the air bubble 506) then passes through the other optical interface 414 before entering the detector light guide 422.

The light passing through the detector light guide 422 can then pass to the light detector (not shown in this view) which can generate a signal based on the received light. Referring now to FIG. 6, a view of electrical potential versus time is shown for a sensing system in accordance with various embodiments herein. The varying electrical potential serves as one example of a signal that can be generated based on the light received by the light detector. In this example, a baseline 602 is shown which is indicative of just a typical fluid in the flow path. However, FIG. 6 also shows a negative deviation 604. This can be indicative of an air bubble in the flow path that is absorbing or scattering/refracting some amount of the light or otherwise preventing some amount of the light from entering the detector light guide 422. Thus, in various embodiments, the system and/or a sensor controller thereof can be configured to identify air bubbles based on a deviation in the signals received from the light detector from the baseline 602 level.

Remarkably, it has been found herein that large air bubbles actually generate an upward deviation in the signal over a baseline level before later falling below the baseline level (e.g., a sequence of a positive deviation from baseline following by a negative deviation from the baseline). As such, the size of droplets can be detected by evaluating the signals received and specifically determining if there was only a negative deviation or if there was an initial positive deviation followed by a negative deviation.

Figure 7:
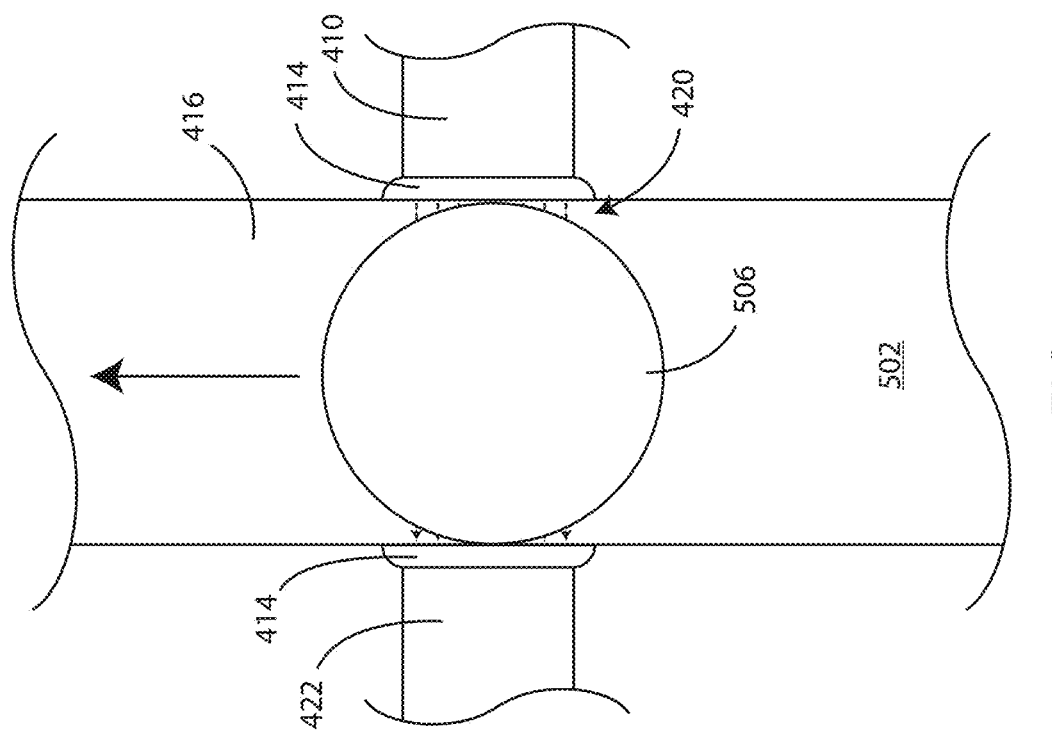
FIG. 7 is a schematic view of a portion of an air bubble sensing system in accordance with various embodiments herein.

Referring now to FIG. 7, a schematic view of a portion of an air bubble sensing system is shown in accordance with various embodiments herein. As before, fluid moves through a flow path 502 defined by the flow cell 416. A light emission 420 from a light source (not shown in this view) passes from the source light guide 410 to the optical interface 414, and then across the flow path 502 wherein it can encounter an air bubble 506. The light emission (as altered by its interactions with the air bubble 506) then passes through the other optical interface 414 before entering the detector light guide 422.

Figure 8:
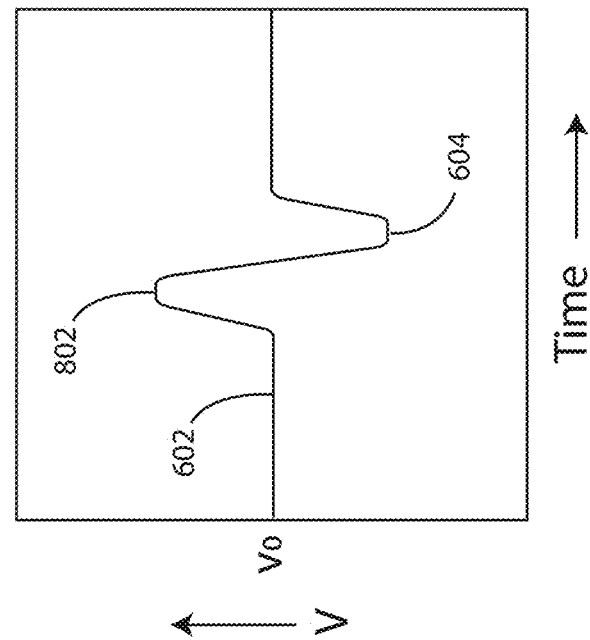
FIG. 8 is a view of potential versus time for a sensing system in accordance with various embodiments herein.

However, this time the negative deviation in the signal is preceded by a positive deviation in the signal. Referring now to FIG. 8, a view of potential versus time for a sensing system is shown in accordance with various embodiments herein. FIG. 8 shows a baseline 602 value that is maintained initially and then a positive deviation 802 followed by a negative deviation 604. This pattern is indicative of a relatively large air bubble as compared with an air bubble that only caused a negative deviation.

Further size information about the air bubbles can also be gathered. For example, an extremely large air bubble can cause a negative deviation (after an initial positive deviation) that holds the sensor signal at the negative value for a period of time that is longer than a smaller droplet.

Figure 9:
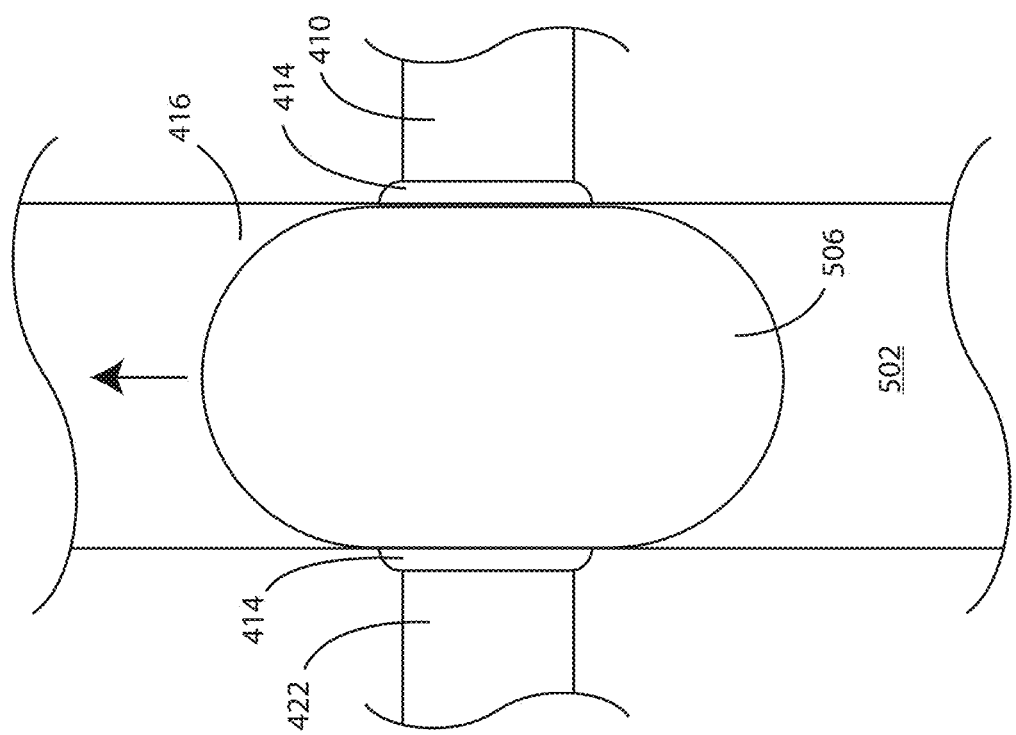
FIG. 9 is a schematic view of a portion of an air bubble sensing system in accordance with various embodiments herein.

Referring now to FIG. 9, a schematic view of a portion of an air bubble sensing system is shown in accordance with various embodiments herein. As before, fluid moves through a flow path 502 defined by the flow cell 416. A light emission 420 from a light source (not shown in this view) passes from the source light guide 410 to the optical interface 414, and then across the flow path 502 wherein it can encounter an air bubble 506. The light emission (as altered by its interactions with the air bubble 506) then passes through the other optical interface 414 before entering the detector light guide 422.

Figure 10:
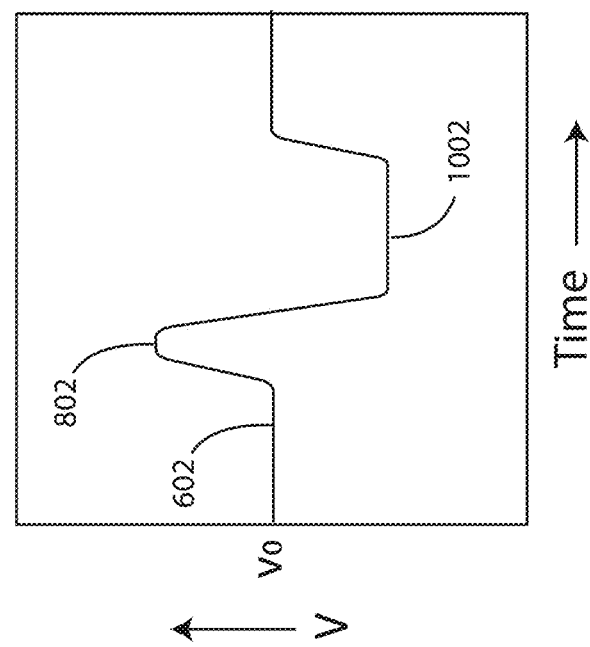
FIG. 10 is a view of potential versus time for a sensing system in accordance with various embodiments herein.

FIG. 10 shows a view of electrical potential versus time for the sensing system is shown in accordance with various embodiments herein. FIG. 10 shows a baseline 602 being maintained initially followed by a positive deviation 802 and an extended negative deviation 1002.

Figure 11:
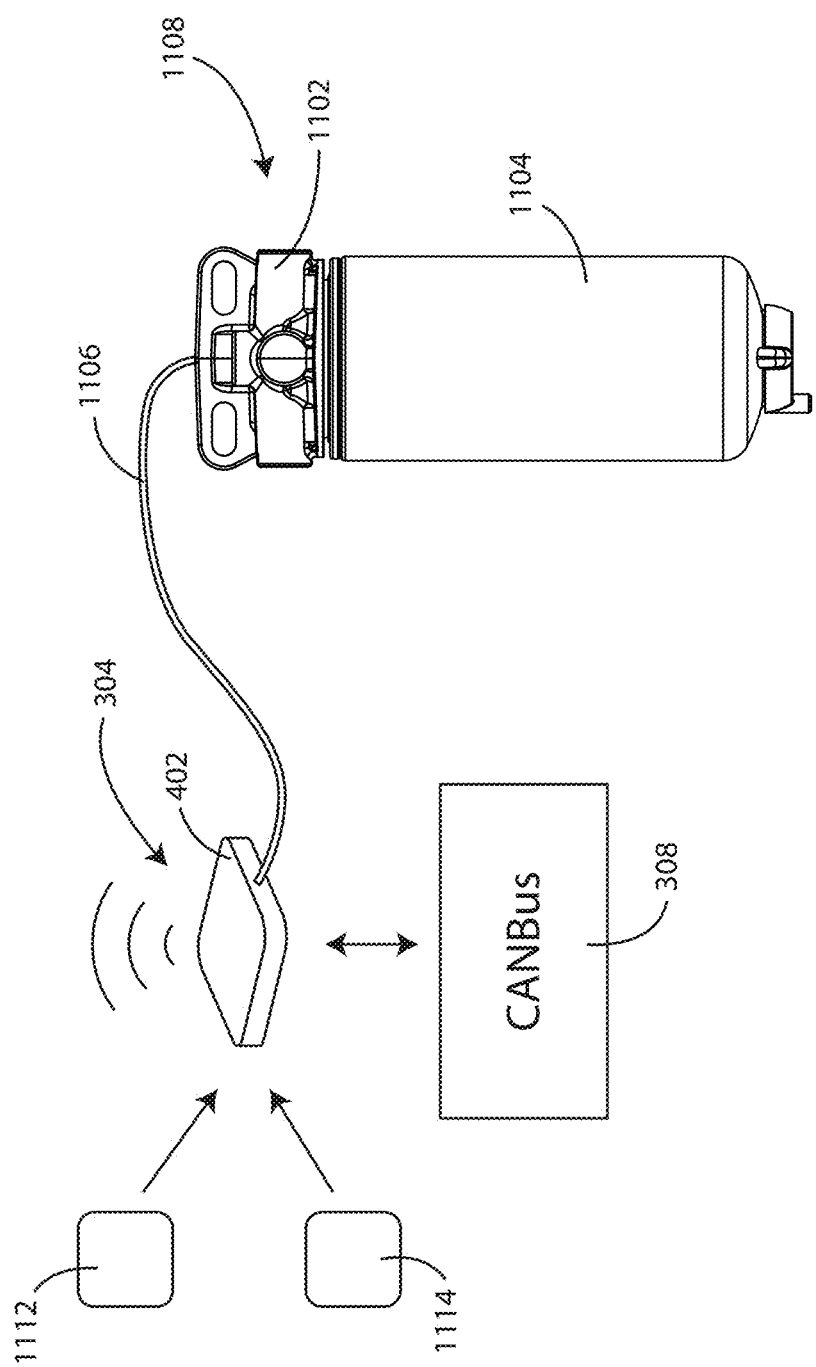
FIG. 11 is a schematic view of an air bubble sensing system in accordance with various embodiments herein.

Referring now to FIG. 11, a schematic view of components of a system herein are shown in accordance with various embodiments herein. The system can include a fluid filter system 1108. The fluid filter system 1108 can include a filter head 1102 and a filter unit 1104. The fluid filter system 1108 can be for filtering fuel, hydraulic fluid, lubricants, coolants, and the like. The fluid filter system 1108 can specifically be for filtering various liquids. In some embodiments, the fluid filter system 1108 can be on a vehicle, but in some embodiments can be on a non-vehicular piece of equipment.

FIG. 11 also shows a housing 402 of an air bubble sensing system 304. The housing 402 can be connected to the fluid filter system 1108 via control cable 1106, which can include electrical wires and/or optical fibers therein. While FIG. 11 depicts the housing 402 separately from the fluid filter system 1108, it will be appreciated that in various embodiments herein, the housing 402 or other components of the air bubble sensing system 304 can be physically integrated into the fluid filter system 1108 and/or mounted thereon. Further, in some embodiments, the air bubble sensing system 304 does not interface with the fluid filter system 1108, but rather interfaces with the fluid line or a component connected to the fluid line at a different point of the fluid system.

The air bubble sensing system 304 can include one or more components or sensor devices and/or can be configured to receive data from one or more components or sensor devices. By way of example, the air bubble sensing system 304 can interface with vehicular data network 308. In some embodiments, the vehicular data network 308 can be a CANBus network. However, the vehicular data network 308 can also be (or connect to) other types of data networks. Interface with a vehicular data network can be via wired or wireless protocols.

In some embodiments, air bubble sensing system 304 can be in communication with a first additional data generating or receiving device 1112 and/or a second additional data generating or receiving device 1114. Data can include, but are not limited to, fluid age, fluid temperature, fluid viscosity, one or more of geolocation and/or altitude data, weather data, temperature data, pressure data, humidity data, fluid filter model number, engine model number, driver ID, and detected servicing, refilling, and/or refueling times.

In some the air bubble sensing system 304 can also include other types of contaminant sensors. For example, the first or second additional data generating and/or receiving device can include or can be in communication with another type of fluid contaminant sensor. In various embodiments herein, the system can then correlate servicing, refilling, or refueling locations with subsequent changes in the contaminant levels as identified (at least partially) by a contaminant sensor to identify an effect of specific locations on contaminant levels and therefore on the amount of contaminants in the fluid. Such contaminant sensors can include, but are not limited to, on-vehicle particulate counters/monitors. In some embodiments, the contaminant sensor can include an optical-based sensor that uses detection of light blocking for particle detection. For example, particles can pass through an optical flow cell including a lighter emitter. The particles can block portions of the light, creating a shadow. These shadows can be detected by a light detector. Contaminant sensors can also rely upon other methods of detection other than light based optical systems. For example, contaminant sensors can also rely upon electrical, magnetic, weight, and/or density properties in order to detect contaminants. In some embodiments, a contaminant sensor herein can detect particles in accordance with ISO 11171 regarding particle count data in fluids. It will be appreciated that data from other types of contaminant sensors (and specifically data from particulate counters/monitors) can be used in isolation or in combination with other types of contaminant data or restriction data discussed herein.

Figure 12:
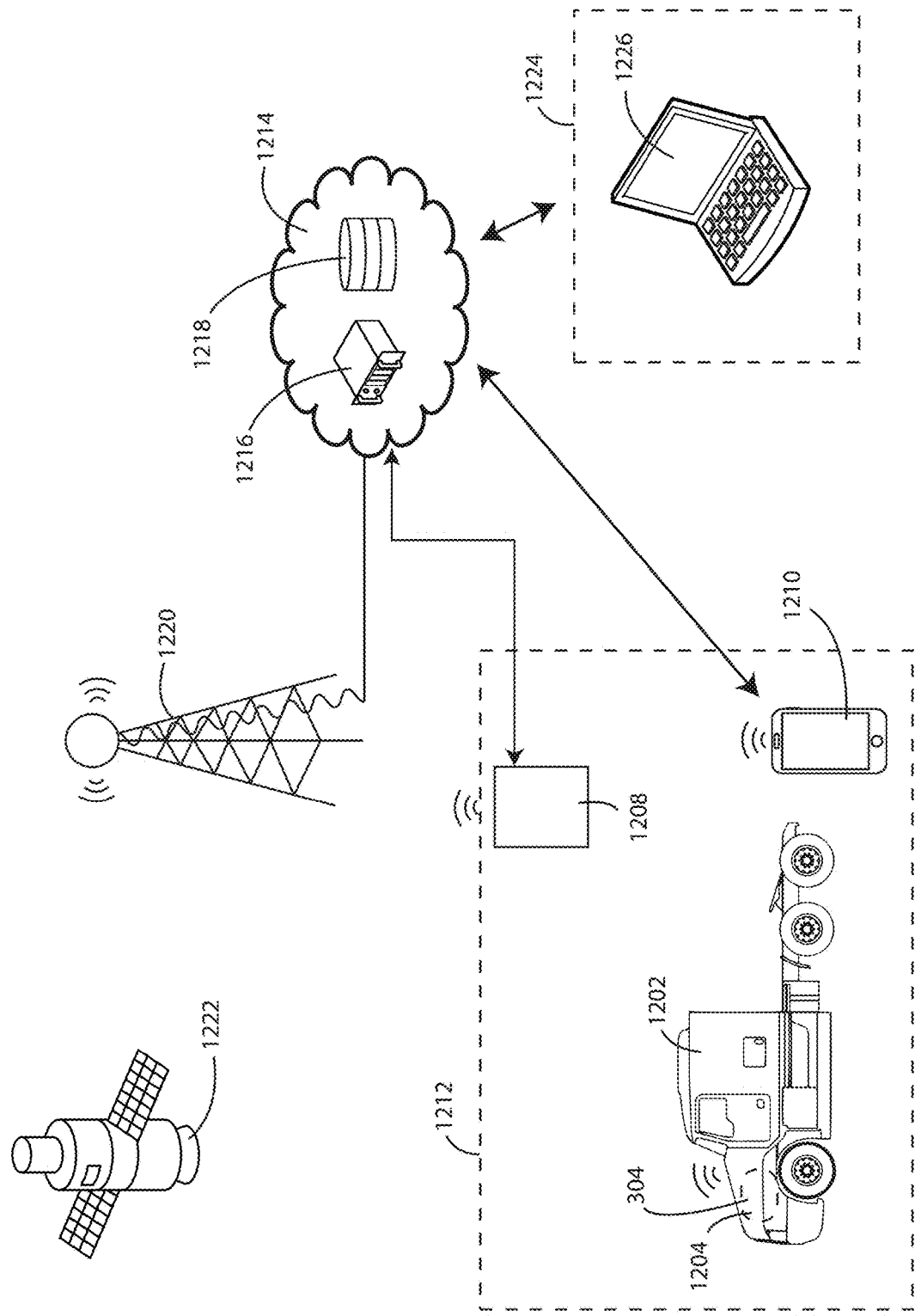
FIG. 12 is a schematic view of an air bubble sensing system in accordance with various embodiments herein.

Referring now to FIG. 12, a schematic view of a system is shown in accordance with various embodiments herein. FIG. 12 shows a vehicle 1202 at a service location 1212. The vehicle 1202 includes a fluid system 1204 (which can be a fuel system, a hydraulic fluid system, a lubricant system, a coolant system, or the like) including an air bubble sensing system 304.

In some cases, the air bubble sensing system 304 can be capable of direct wireless data communication to the cloud 122 or to another data network. In some cases, the air bubble sensing system 304 can be capable of indirect wireless data communication to the cloud 122 or to another data network. In some embodiments, the air bubble sensing system 304 can communicate with a cell tower 1220, which in turn can relay data communications back and forth with the cloud 1214 and components thereof such as servers 1216 (real or virtual) and databases 1218 (real or virtual).

Wireless communication can take place using various protocols. For example, wireless communications/signals exchanged between the air bubble sensing system 304 and/or the air bubble sensing system and the cloud 1214 (or between components of the air bubble sensing system 304 and/or the air bubble sensing system) can follow many different communication protocol standards and can be conducted through radiofrequency transmissions, inductively, magnetically, optically, or even through a wired connection in some embodiments. In some embodiments herein, IEEE 802.11 (e.g., WIFI®), BLUETOOTH® (e.g., BLE, BLUETOOTH® 4.2 or 5.0), ZIGBEE®, or a cellular transmission protocol/platform can be used such as CDMA, cdmaOne, CDMA2000, TDMA, GSM, IS-95, LTE, 5G, GPRS, EV-DO, EDGE, UMTS, HSDPA, HSUPA, HSPA+, TD-SCDMA, WiMAX, Micro.Sp, and the like. In various embodiments, a different standard or proprietary wireless communication protocol can also be used.

As referenced, cloud 1214 resources may include databases 1218. Such databases 1218 can store various pieces of information including, but not limited to, fluid service location data (such as service location IDs, service location geolocation and/or altitude data, service location visit data, service location filter loading impact data, and the like), refueling location data (such as refueling location IDs, refueling location geolocation and/or altitude data, fuel filter loading rate data related to specific refueling locations, refueling location estimated impurity/contamination information, refueling location visit data, refueling location filter loading impact data, and the like), fleet data, vehicle data, filtration system data, and the like.

It will be appreciated that database content may be spread across many different physical systems, devices, and locations. Further, while not depicted in FIG. 12, it will be appreciated that database records can also be stored at the level of the air bubble sensing system 304. In various embodiments, the database 1218 or portions thereof can be stored at a location remote from other components of the system, such as the air bubble sensing system 304. In some embodiments, records or portions of the database can be stored across different physical locations and, in some embodiments, cached across different physical locations for ready access.

In some embodiments, the service location 1212 can include a location communication device 1208. The location communication device 1208 can include various components. In some embodiments, the location communication device 1208 can be a wireless data gateway, including components such as a router and/or other data networking hardware. In some cases, the air bubble sensing system 304 can be in wireless communication with the location communication device 1208 in order to provide communication with the cloud 1214 or another data network. In some cases, the air bubble sensing system 304 can receive information from the location communication device 1208 such as geolocation and/or altitude data (which can include latitude/longitude coordinates amongst other things), or other location identifying information such as a nearest address, nearest landmark, etc. As used herein, the term "geolocation data" shall include reference to all location identifying data, unless the context dictates otherwise.

In some cases, geolocation data can be derived from a satellite 1222 based geolocation system. Such systems can include, but are not limited to, GPS L1/L2, GLONASS G1/G2, BeiDou B1/B2, Galileo E1/E5b, SBAS, or the like. In various embodiments, the system can include a geolocation circuit (described below) that can include appropriate signal receivers or transceivers to interface with a satellite 1222 and/or the geolocation circuit can interface with and/or receive data from a separate device or system that provides geolocation data or derives geolocation data from a satellite 1222 or other device. However, it will be appreciated that geolocation data herein is not limited to just that which can be received from or derived from interface with a satellite 1222. Geolocation data can also be derived from addresses, beacons, landmarks, various referential techniques, IP address evaluation, and the like. Altitude can be measured directly using an altimeter or similar sensor, or can be derived based on geolocation data assuming the vehicle or other equipment for which air bubbles are being measured is at ground level.

In various embodiments, the air bubble sensing system 304 can also include and/or can be in communication with a mobile communications/guidance device 1210. In some cases, the mobile communications/guidance device 1210 can be used to provide data communication for the air bubble sensing system 304 and the cloud or another data network. In various embodiments, the mobile communications/guidance device 1210 can provide outputs to or inputs from the vehicle 1202 or a driver of the vehicle 1202. In some cases, the mobile communications device can be used to provide recommendations (visually, audibly, and/or haptically) to the driver of the vehicle. For example, in various embodiments, a recommendation can be generated by the system and can be forwarded to a mobile communications/guidance device 1210 associated with a vehicle 1202 or a driver of a vehicle 1202. In various embodiments herein, the system can be configured to generate recommendations for a vehicle 1202 driver based on detected air bubbles. In various embodiments, the recommendations include at least one of a recommended service location, a recommended filter type, a recommended service time, and a recommended vehicle service.

Specific recommendations/reports generated by the system can include specific points of information. However, as merely one example, the air bubble sensing system 304 and/or components thereof can be configured to generate a report relating to different service locations (and/or patterns of the same). As another specific example, the air bubble sensing system 304 and/or components thereof can be configured to generate a report that profiles the frequency with which different drivers in a fleet use recommended and dis-recommended service.

In some embodiments the mobile communications/guidance device 1210 can be, for example, a smart phone, or another type of computing device including wireless communication capabilities. In some embodiments the mobile communications/guidance device 1210 can be a vehicle navigation system.

In some embodiments, the air bubble sensing system 304 can also include and/or be in communication with a fleet monitoring center 1224 (real or virtual). The fleet monitoring center 1224 can include a remote computing device 1226 and can receive information and/or recommendation about specific vehicles and/or specific service locations. In some cases, the air bubble sensing system 304 can be used to provide recommendations to a fleet control operator at the fleet monitoring center 1224 and/or receive information or instructions from a fleet control operator at the fleet monitoring center 1224.

In various embodiments, systems described herein can also serve as, or function as, or be a service guidance system for a vehicle 1202. For example, the air bubble sensing system 304 and/or components thereof can be configured to query a database 1218 that can include records of specific service locations. The air bubble sensing system 304 can be configured to provide at least one of route and service site recommendations to a user output device.

Figure 13:
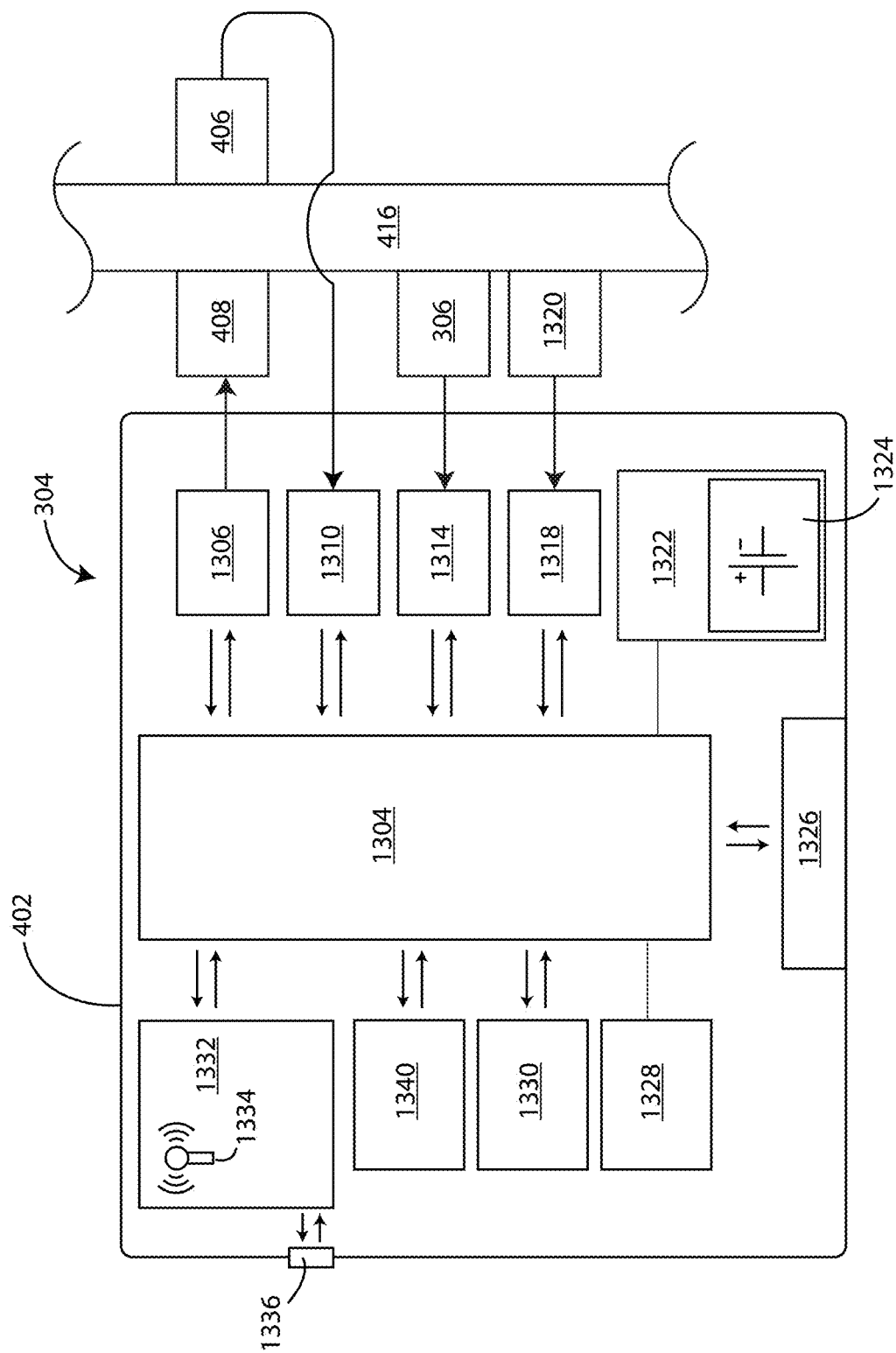
FIG. 13 is a block diagram of components of an air bubble sensing system in accordance with various embodiments herein.

Referring now to FIG. 13, a block diagram of components of an air bubble sensing system 304 is shown in accordance with various embodiments herein. However, it will be appreciated that a greater or lesser number of components can be included with various embodiments and that this schematic diagram is merely illustrative. The air bubble sensing system 304 includes a housing 402 and a sensor controller 1304 or ("control circuit" or "system control circuit"). The sensor controller 1304 can include various electronic components including, but not limited to, a microprocessor, a microcontroller, a FPGA (field programmable gate array) chip, an application specific integrated circuit (ASIC), or the like. The sensor controller 1304 can execute various operations as described herein. However, it will be appreciated that operations herein can be executed across multiple devices with separate physical circuits, processors, or controllers with different operations being performed redundantly or divided across different physical devices. As such, some operations may be performed (in whole or in part) at the edge, such as by a circuit/processor/controller associated with an air bubble sensing system 304 while other operations may be performed (in whole or in part) by a separate device or in the cloud.

The air bubble sensing system 304 can include a light source 408 and a light detector 406. Both the light source 408 and the light detector 406 can be associated with the flow cell 416. The light source 408 can be in communication with a light source controller 1306. The light detector 406 can be in communication with a light detector channel interface 1310.

In various embodiments, the air bubble sensing system 304 can include and/or be in communication with a flow rate sensor 306 and a flow sensor channel interface 1314. In various embodiments, the air bubble sensing system 304 can include and/or be in communication with another type of sensor, such as temperature sensor 1320 and a temperature sensor channel interface 1318. Other types of sensors herein can include vibration sensors, flow sensors, pressure sensors, and the like.

The channel interfaces can include various components such as amplifiers, analog-to-digital converters (ADCs), digital-to-analog converters (DACs), digital signal processors (DSPs), filters (high-pass, low-pass, band-pass) and the like. In some cases, the channel interfaces may not exist as discrete components but, rather, can be integrated into the sensor controller 1304.

Temperature sensors herein can be of various types. In some embodiments, the temperature sensor 1320 can be a thermistor, a resistance temperature device (RTD), a thermocouple, a semiconductor temperature sensor, or the like.

In some embodiments, one or more temperature sensors herein can be configured to measure a temperature of a light source and/or light detector herein. As such, the signal of the light detector can be corrected for temperature effects (e.g., the signal can be normalized). This can be performed in various ways. In one approach, an empirically derived (or otherwise obtained) standard curve or calibration curve relating light output of the light source and/or voltage output of the light detector with temperature can be applied to normalize the signals of the light detector. In some approaches, an equation relating light detector voltage output with temperature over a range of operating temperatures can be used to correct or normalize the signals of the light detector for temperature.

In some embodiments, one or more pressure sensors can also be included herein. Pressure sensors herein can be of various types. The pressure sensors can include, but are not limited to, strain gauge type pressure sensors, capacitive type pressure sensors, piezoelectric type pressure sensors, and the like. In some embodiments, pressure sensors herein can be MEMS-based pressure sensors. In various embodiments, the pressure sensor can be a high-speed (e.g., high sample rate) pressure sensor. In various embodiments the high-speed pressure sensor can sample at rates of 1,000, 1,500, 2,000, 2,500, 3,000, 5,000, 10,000, 15,000, 20,000 Hz or higher, or at a rate falling within a range between any of the foregoing. In various embodiments the high-speed pressure sensor can have a response time of less than 10, 5, 2.5, 1, 0.5, 0.25, 0.1, 0.05 or 0.01 milliseconds, or a response time falling within a range between any of the foregoing.

The processing power of the sensor controller 1304 and components thereof can be sufficient to perform various operations including various operations on signals/data from sensors or other components including, but not limited to averaging, time-averaging, statistical analysis, normalizing, aggregating, sorting, deleting, traversing, transforming, condensing (such as eliminating selected data and/or converting the data to a less granular form), compressing (such as using a compression algorithm), merging, inserting, time-stamping, filtering, discarding outliers, discarding values exceeding a threshold, calculating trends and trendlines (linear, logarithmic, polynomial, power, exponential, moving average, etc.), normalizing data/signals, executing peak detection and/or peak fitting algorithms, and the like. Fourier analysis can decompose a physical signal into a number of discrete frequencies, or a spectrum of frequencies over a continuous range. In various embodiments herein, operations on signals/data can include Fast Fourier Transformations (FFT) to convert data/signals from a time domain to a frequency domain. Other operations on signals/data here can include spectral estimation, frequency domain analysis, calculation of root mean square acceleration value ($G_{RMS}$), calculation of acceleration spectral density, power spectral densities, Fourier series, Z transforms, resonant frequency determination, harmonic frequency determination, and the like. It will be appreciated that while various of the operations described herein (such as Fast Fourier transforms) can be performed by general-purpose microprocessors, they can also be performed more efficiently by digital signal processors (DSPs) which can, in some embodiments, be integrated with the sensor controller 1304 or may exist as separate, discrete components.

In various embodiments, the air bubble sensing system 304 can include a power supply circuit 1322. In some embodiments, the power supply circuit 1322 can include various components including, but not limited to, a battery 1324, a capacitor, a power-receiver such as a wireless power receiver, a transformer, a rectifier, and the like. In some embodiments, the air bubble sensing system 304 can be configured to run off of engine power or another source of power associated with the equipment that the air bubble sensing system 304 is used with or mounted on.

In various embodiments the air bubble sensing system 304 can include an output device 1326. The output device 1326 can include various components for visual and/or audio output including, but not limited to, lights (such as LED lights), a display screen, a speaker, and the like. In some embodiments, the output device can be used to provide notifications or alerts to a system user such as current system status, an indication of a problem, a required user intervention, a proper time to perform a maintenance action, or the like.

In various embodiments the air bubble sensing system 304 can include memory 1328 and/or a memory controller. The memory can include various types of memory components including dynamic RAM (D-RAM), read only memory (ROM), static RAM (S-RAM), disk storage, flash memory, EEPROM, battery-backed RAM such as S-RAM or D-RAM and any other type of digital data storage component. In some embodiments, the electronic circuit or electronic component includes volatile memory. In some embodiments, the electronic circuit or electronic component includes non-volatile memory. In some embodiments, the electronic circuit or electronic component can include transistors interconnected to provide positive feedback operating as latches or flip flops, providing for circuits that have two or more metastable states, and remain in one of these states until changed by an external input. Data storage can be based on such flip-flop containing circuits. Data storage can also be based on the storage of charge in a capacitor or on other principles. In some embodiments, the non-volatile memory 1328 can be integrated with the sensor controller 1304.

In various embodiments the air bubble sensing system 304 can include a clock circuit 1330. In some embodiments, the clock circuit 1330 can be integrated with the sensor controller 1304. While not shown in FIG. 13, it will be appreciated that various embodiments herein can include a data/communication bus to provide for the transportation of data between components such as an I2C, a serial peripheral interface (SPI), a universal asynchronous receiver/transmitter (UART), or the like. In some embodiments, an analog signal interface can be included. In some embodiments, a digital signal interface can be included.

In various embodiment the air bubble sensing system 304 can include a communications circuit 1332. In various embodiments, the communications circuit can include components such as an antenna 1334, amplifiers, filters, digital to analog and/or analog to digital converters, and the like. In some embodiments, the air bubble sensing system 304 can also include wired input/out interface 1336 for wired communication with other systems/components including, but not limited to one or more vehicle ECUs, a CANBus network, or the like.

Air bubble monitoring systems herein can also include a geolocation and/or altitude circuit 1340. In various embodiments, the geolocation and/or altitude circuit 1340 can be configured to generate or receive geolocation and/or altitude data. In various embodiments, the geolocation and/or altitude circuit 1340 can receive geolocation and/or altitude data from a separate device. In various embodiments, the geolocation and/or altitude circuit 1340 can infer geolocation based on detection of a wireless signal (such as a WIFI signal, a cell tower signal, or the like). In various embodiments, the geolocation and/or altitude circuit 1340 can include a satellite communications circuit. In various embodiments, the geolocation and/or altitude circuit 1340 can include or be in communication with an altimeter or similar sensor.

The system and/or the sensor controller 1304 can be configured to make various calculations as described herein. For example, in various embodiments, the sensor controller 1304 can, using inputs as described herein, be configured to estimate the amount of air bubble. It will be appreciated that references to air bubble herein shall refer to free air unless the context dictates otherwise. Many other calculations that can be executed by the sensor controller 1304 and/or other components of the system are described in greater detail below.

Estimating Amount of Air in Fluid

As described herein, the system can be configured to estimate the amount of air in fluids. Such estimates can be based on various inputs or estimates including one or more of the number of air bubbles detected per unit time (N), the average size/volume of air bubbles detected (V), the flow rate of fluid through the sensor (F), a sampling factor (S) (if no sampling bias is present this would be equal to 1) and the like. In one approach, the amount of air (as air bubbles) in fluid can be estimated and described as the fraction of air in fluid according to the following equation:

$$AIF = \frac{N * V * S}{F}$$

The number of air bubbles detected per unit time can be directly detected by the sensor(s) of a water in fluid sensing system herein as described and as illustrated with respect to the examples below.

The size/volume of air bubbles detected can be estimated as described above based on the optical signals such as described with respect to FIGS. 5-10.

The flow rate of fluid can be measured/determined/estimated in various ways. In some embodiments, the system can include a flow rate sensor producing a value for flow rate of fluid. In some embodiments, the system can receive data on fluid flow rate from a vehicular data network, such as CANBus or the like.

In some embodiments, a value for flow rate can be estimated pipe flow equations and information regarding the pressure drop between two points. In specific, a relationship between flow rate and pressure drop exist that can be used in order to estimate a flow rate. Thus, in some embodiments, herein measures of pressure upstream and downstream from where the air bubbles are detected can be used to estimate the flow rate of fluid. In some embodiments, the relationship between pressure drop and flow rate can be determined empirically and then programmed into the system or a component thereof.

In some embodiments, a relationship between pressure drop and flow rate through a flow cell or fluid line herein can be determined empirically for water and then modified for use with another fluid type. By way of example, the following equation can be used where values P1 and P2 are determined empirically for water, and where $P_{S,F}$ is the pressure drop across the sensor when the fluid is another fluid, $\mu_W$ and $\mu_F$ are the dynamic viscosities of water (1 cP) and another fluid (e.g., ~2.5 cP in the case of a hydrocarbon fuel as merely one example) respectively, and $U_{S,W}$ is the fluid flow rate through the sensor:

$$P_{S,F} = \frac{\mu_W}{\mu_F} P_{S,W} = \frac{\mu_W}{\mu_F}(P1 * U_{S,F} - P2)$$

In some embodiments, a relationship can exist between the total number of air bubbles detected per unit time as normalized by a flow rate of fluid and the amount of air bubbles in the fluid. As such, in some embodiments, data regarding the number of air bubbles detected by the sensor(s) of an air bubble sensing system herein can be combined with data regarding a flow rate of fluid in order to generate an estimate of the amount of air bubbles in the fluid. In some embodiments, a fluid flow rate can be estimated from the analysis of bubble size distribution and peak width.

It will be appreciated that there can be significance associated with whether a level of air bubbles is merely short-term (acute) or long-term (chronic). This significance can apply to determining possible sources of aeration in fluids as well as the relative risk of damage to the vehicle posed. For example, if a high level of aeration in a fluid exists only acutely, then this may point to a cause such as a recently developed air leak. In contrast, if a high level of air bubbles is detected chronically, then this may point to another cause.

There can also be significance associated with patterns (time, geography, etc.) of detected amounts of air bubbles in fluid.

In various embodiments herein, machine learning algorithms can be used to derive patterns between estimated amounts of air bubbles in fluids and other pieces of information available to the system including, but not limited to, geolocation and/or altitude of service locations, time of events, ambient temperature, ambient humidity, weather conditions, vehicle operator identity, routes traveled, and the like.

Machine learning algorithms used herein can include, but are not limited to, supervised learning and unsupervised learning algorithms. Machine learning algorithms used herein can include, but are not limited to, classification algorithms (supervised algorithms predicting categorical labels), clustering algorithms (unsupervised algorithms predicting categorical labels), ensemble learning algorithms (supervised meta-algorithms for combining multiple learning algorithms together), general algorithms for predicting arbitrarily-structured sets of labels, multilinear subspace learning algorithms (predicting labels of multidimensional data using tensor representations), real-valued sequence labeling algorithms (predicting sequences of real-valued labels), regression algorithms (predicting real-valued labels), and sequence labeling algorithms (predicting sequences of categorical labels).

Machine learning algorithms herein can also include parametric algorithms (such as linear discriminant analysis, quadratic discriminant analysis, and maximum entropy classifier) and nonparametric algorithms (such as decision trees, kernel estimation, naïve Bayes classifier, neural networks, perceptrons, and support vector machines). Clustering algorithms herein can include categorical mixture models, deep learning methods, hierarchical clustering, K-means clustering, correlation clustering, and kernel principal component analysis. Ensemble learning algorithms herein can include boosting, bootstrap aggregating, ensemble averaging, and mixture of experts. General algorithms for predicting arbitrarily structured sets of labels herein can include Bayesian networks and Markov random fields. Multilinear subspace learning algorithms herein can include multilinear principal component analysis (MPCA). Real-valued sequence labeling algorithms can include Kalman filters and particle filters. Regression algorithms herein can include both supervised (such as Gaussian process regression, linear regression, neural networks and deep learning methods) and unsupervised (such as independent component analysis and principal components analysis) approaches. Sequence labeling algorithms herein can include both supervised (such as conditional random fields, hidden Markov models, maximum entropy Markov models, and recurrent neural networks) and unsupervised (hidden Markov models and dynamic time warping) approaches.

In some embodiments, various actions/operations of the system can be triggered by an estimated amount of air bubbles crossing a threshold value. In some embodiments, these threshold values can be predetermined and/or fixed. In other embodiments, these threshold values can be dynamic.

In some embodiments, the system can distinguish between an estimated amount of air bubbles in fluid creating a need to stop vehicle operation immediately versus an estimated amount of air bubbles in fluid allowing continued operation. In one example, distinguishing between these different categories can be performed according to threshold values. Different categories of estimated air bubbles amounts can also be reflected in qualitative notifications sent to a vehicle operator, a fleet controller, or another person or system. For example, in some embodiments, a notification can be sent that can reflect either a "high", "medium", or "low" amount of estimated air bubbles in fluid.

In some embodiments, the threshold values may be different depending on whether the estimated amount of air or air bubbles is only short term (acute or transitory) versus long-term (chronic). In various embodiments, the threshold values may be higher for short term values versus long term values.

Mitigating Effect of Water Droplets

In some instances, water droplets may be present in a fluid line of a system. It has been found herein that since water has a different refractive index than other vehicular or system fluids, light can be scattered and reflected off the interface (between a system fluid and a water droplet) or otherwise transmitted and refracted through the interface. This leads to less light reaching the sensor detector and gives the appearance of a light absorbance event. Therefore, water droplets can also generate what appear to be absorbance peaks and therefore can potentially be confused with air bubbles making the presence of water droplets a potential source of error when measuring air bubbles in a fluid line.

However, various embodiments herein can be configured to prevent the presence of water droplets from interfering with the measurement of air bubbles in fluids. In some embodiments, signal processing approaches can be used to distinguish between water droplets and air bubbles. In specific, air bubbles have been found to generate what appear to be absorbance peaks of greater absorbance magnitude and peak width. As such, signal processing techniques can be used in accordance with systems herein to prevent the presence of water droplets from interfering with the measurement of air bubbles in fluids. For example, in some embodiments, the system can be configured to exclude peaks crossing a threshold value for absorbance magnitude and/or peak width when calculating the amount of air bubbles in fluids. The threshold value can be an absolute value or a relative value. In some embodiments, the threshold value can be a statistical measure such as an average value, a standard deviation value of a distribution, a percentile value, or the like.

Other techniques can also be used to mitigate the effects of water droplets on the measurement of air bubbles in fluids. In some embodiments, a secondary detector can be used to determine an amount of light reflected which distinguishes between water droplets and air bubbles. For example, in some embodiments, the system can be configured to measure absorbance at two different wavelengths of light (for example, using a first light source configured to emit near-infrared light and a second light source configured to emit light within the visible spectrum) and distinguish between water droplets and air bubbles by comparing the absorbance peaks generated at one wavelength versus the other.

Figure 14:
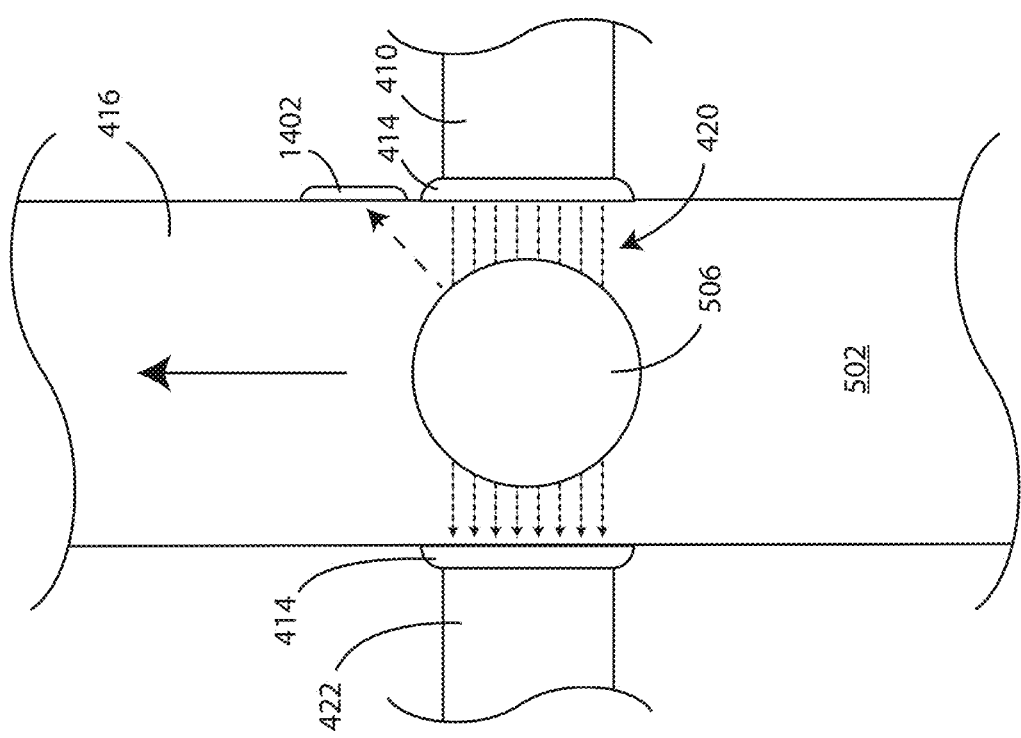
FIG. 14 is a schematic view of a portion of an air bubble sensing system in accordance with various embodiments herein.

In some embodiments, a secondary detector can be used to determine an amount of light reflected which distinguishes between water droplets and air bubbles. Referring now to FIG. 14, a schematic view is shown of a portion of an air bubble sensing system in accordance with various embodiments herein. FIG. 14 is generally similar to FIG. 5 described above. However, in this embodiment, a secondary detector 1402 is included and is positioned to be able to detect reflected light from air bubble passing through the sensor.

Methods

Many different methods are contemplated herein, including, but not limited to, methods of detecting air bubbles, methods of monitoring aeration of fluids, methods of detecting pressures, methods of monitoring vehicle operation, and the like. Aspects of system/device operation described elsewhere herein can be performed as operations of one or more methods in accordance with various embodiments herein.

In an embodiment, a method of determining a level of restriction of a filter is included, the method can include evaluating signals received from a light detector, detecting air bubbles based on the signals received from the light detector, and generating an estimate of a restriction level of a liquid filter upstream from the light detector based on the detected air bubbles.

In an embodiment of the method, the light detector is disposed within a fluid system (fuel system, hydraulic fluid system, lubricant system, etc.) at an area under vacuum pressure. In an embodiment of the method, the light detector is disposed within a fluid system downstream from the filter and upstream from a fluid pump although other positions of the light detector with respect to filter(s) and pump(s) are also contemplated herein.

In an embodiment, the method can further include distinguishing between air bubbles and water droplets in a fluid based on at least one of peak magnitude and peak width. In an embodiment, the method can further include distinguishing between air bubbles and water droplets based on a ratio of peak magnitude to peak width. In an embodiment, the method can further include distinguishing between air bubbles and water droplets based on peak magnitude. In an embodiment, the method can further include distinguishing between air bubbles and water droplets based on a magnitude of a reflection peak prior to an absorbance peak.

In an embodiment, the method can further include emitting light into a sampling channel. In an embodiment of the method, emitting light into a sampling channel further comprises emitting near-infrared light.

In an embodiment, the method can further include generating an estimate of a restriction level of a fluid filter upstream from the light detector based on one or more properties of detected air bubbles. In an embodiment of the method, generating an estimate of a restriction level of a fluid filter upstream from the light detector based on one or more the properties of detected air bubbles further comprises generating the estimate of a restriction level using a fluid flow rate through the filter.

In an embodiment, the method can further include determining an end of life of the fluid filter based on the estimated restriction level of the fluid filter.

In an embodiment, the method can further include initiating generation of an alert if a number of detected air bubbles exceeds a threshold value over a baseline value.

In an embodiment, the method can further include tracking a number of detected air bubbles over time.

In an embodiment, a method of estimating an amount of air in a hydraulic fluid line is included, the method including detecting air bubbles based on the signals received from a light detector and estimating an amount of air in a hydraulic fluid line based on the detected air bubbles.

In an embodiment, the method can further include initiating generation of an alert if a number of detected air bubbles exceeds a threshold value. In an embodiment, the method can further include initiating generation of an alert if a total volume of air bubbles exceeds a threshold value. In an embodiment, the method can further include tracking a number of detected air bubbles over time.

In an embodiment, a method of estimating an amount of pressure in a fluid line is included, the method including detecting air bubbles based on the signals received from a light detector, and estimating an amount of pressure in a fluid line based on the detected air bubbles.

Aspects may be better understood with reference to the following examples. These examples are intended to be representative of specific embodiments but are not intended as limiting the overall scope of embodiments herein.

EXAMPLES

Example 1: Detection of Air Bubbles in Fuel

An air bubble sensing system was set up consistent with that shown in FIG. 3. In specific, a sensing system was prepared with a 300 um ID borosilicate glass flow cell. The light source was a near-infrared LED (1550 nm; Thor Labs) and was focused on the channel with a 200 um fiber optic cable (Thor Labs). The light was detected with a variable gain InGaAs detector set at 60 dB of gain (Thor Labs). Light was collected and delivered to the detector with a 400 um fiber optic cable. The flow cell was encased in a machined aluminum body, designed to sample a portion of the main flow.

The air bubble sensing system was placed on a test bench that mimics the performance of a fuel filter under suction. The bench consisted of a filter housing, which can contain a filter or be an empty housing, a valve to add artificial restriction upstream of the filter housing, and a pump downstream of the filter housing and valve. The sensor is placed between the filter housing and pump. Air was created in the fuel sample by vacuum pressure. The filter acts as restriction and a nucleation site and can change the size and amount of air in the fuel. A dP sensor was placed across the valve/filter housing assembly to monitor the effective filter restriction. The bench was run at various flow-rates and valve restrictions. The signal from the light detector was recorded. Signal processing and peak identification was completed in MATLAB using standard peak fitting algorithms.

Figure 15:
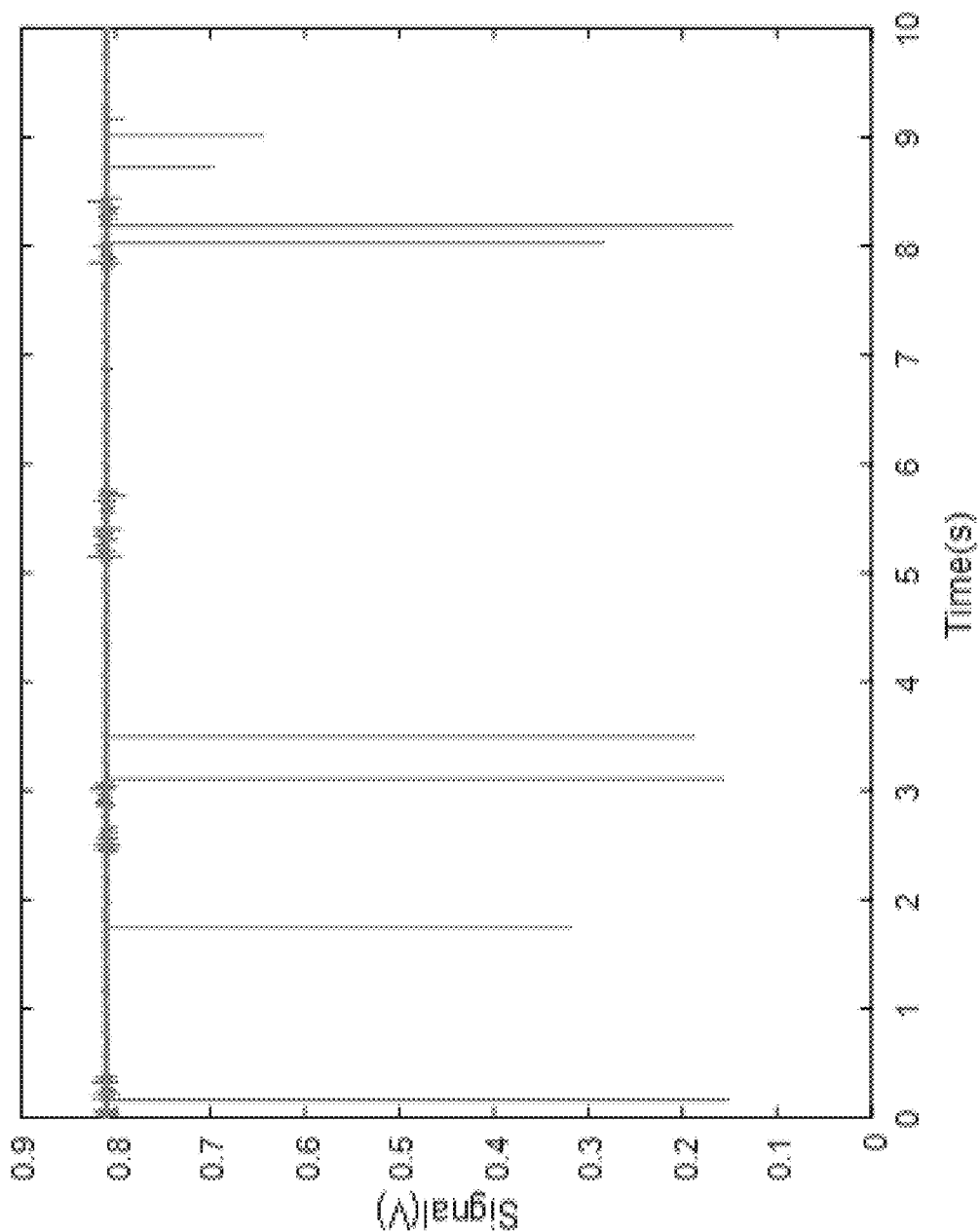
FIG. 15 is a view of potential versus time for a sensing system in accordance with various embodiments herein.

FIG. 15 shows the signal when the flow was 4 lpm with a clean filter (Donaldson P591392) and no additional restriction from the valve (valve/filter assembly dP=0.71 PSI). The large peaks observed are air bubbles; the small peaks are electronic noise also present in a control experiment with no flow. This shows that a system herein can be used to obtain a count of air bubbles over time.

Example 2: Air Bubble Count Differences with Restriction and/or No Filter

An air bubble sensing system was set up consistent with that shown in FIG. 3. In specific, a sensing system was prepared with a 300 um ID borosilicate glass flow cell. The light source was a near-infrared LED (1550 nm; Thor Labs) and was focused on the channel with a 200 um fiber optic cable (Thor Labs). The light was detected with a variable gain InGaAs detector set at 60 dB of gain (Thor Labs). Light was collected and delivered to the detector with a 400 um fiber optic cable. The flow cell was encased in a machined aluminum body, designed to sample a portion of the main flow.

The air bubble sensing system was placed on a test bench that mimics the performance of a fuel filter under suction. The bench consisted of a filter housing, which can contain a filter or be an empty housing, a valve to add artificial restriction upstream of the filter housing, and a pump downstream of the filter housing and valve. The sensor is placed between the filter housing and pump. Air was created in the fuel sample by vacuum pressure. The filter acts as restriction and a nucleation site and can change the size and amount of air in the fuel. A dP sensor was placed across the valve/filter housing assembly to monitor the effective filter restriction. The bench was run at various flow-rates and valve restrictions. The signal from the light detector was recorded. Signal processing and peak identification was completed in MATLAB using standard peak fitting algorithms.

| Test | Filter | Flowrate (1 pm) | Additional Restriction | Filer/Valve dP (PSI) | Reflection Peaks/Minute* | Absorbance/Refraction Peaks per Minute* |
|---|---|---|---|---|---|---|
| 1 | None | 4 | No | 0.55 | 2,968 | 1,868 |
| 2 | P581392 | 4 | No | 0.71 | 42 | 24 |
| 3 | P581392 | 3 | No | 0.35 | 4 | 0 |
| 4 | P581392 | 3 | Yes | 1.70 | 315 | 346 |

*Noise peaks subtracted from controls run without flow.

This data shows that the addition of restriction to a filter under suction increases the number of air bubbles being detected. The data further shows that the absence of a filter leads to a greater number of peaks. These air bubbles are generally smaller and can be used to determine if no filter is installed.

Example 5: Distinguishing Air Bubbles from Water Droplets

An air bubble sensing system was set up consistent with that shown in FIG. 3 and as described in Example 2. The sensor was placed on a fuel-water separation test bench typically used for testing water removal filters according to standard methods. In one instance, the system was set up such that water droplets (d50=75 μm, 500 ppm) would be received by the sensor. In another instance, the sensor was placed on a fuel test bench described in Example 1 where the system was set up such that air bubbles would be received by the sensor. The main flow operated at 3 L/min and consisted of diesel fuel. Signal data was captured with a data acquisition system. Signal processing and peak identification was completed in MATLAB using standard peak fitting algorithms.

Figure 16:
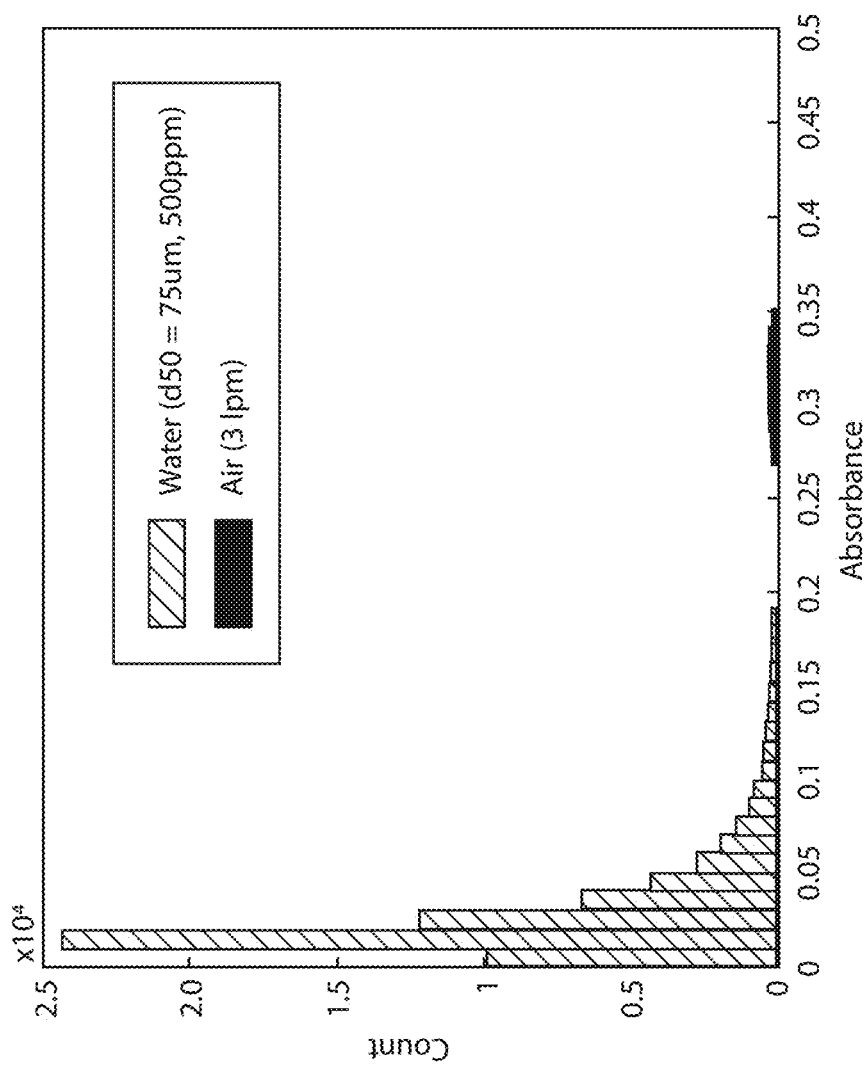
FIG. 16 is a histogram showing counts of peaks at different absorbance levels for water droplets and air bubbles in a system herein.
Figure 17:
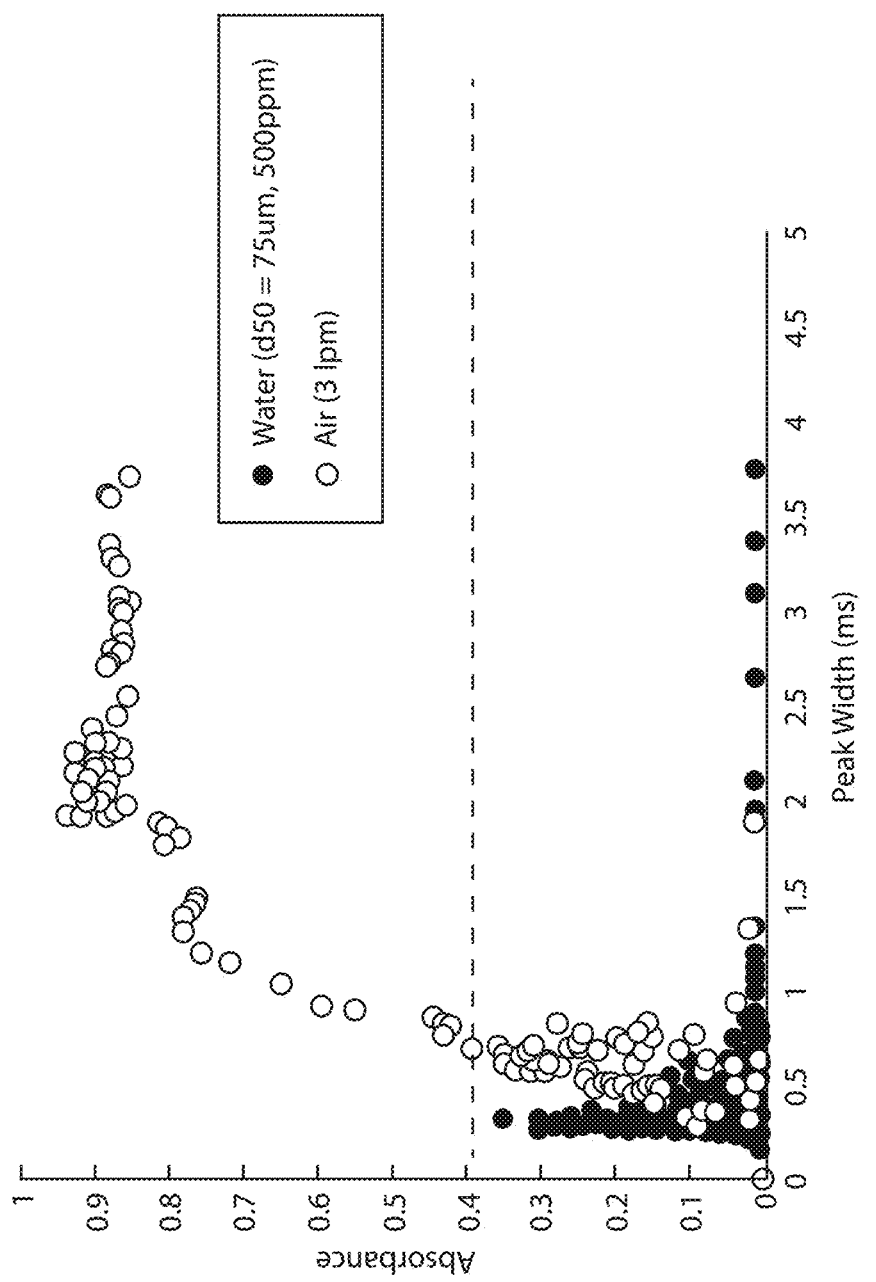
FIG. 17 is a graph showing the relationship between absorbance and peak width for water droplets and air bubbles in a system herein.

In FIG. 16, a histogram is shown of the counts of peaks at different absorbance levels for 15 minutes of data through the test system. It can be seen that the distribution of air peaks generated substantially larger absorbance values than did water droplets. Similarly, referring to FIG. 17, a graph showing the relationship between absorbance and peak width is shown for 30 seconds of data. It can be seen that the air bubbles generated substantially larger peak widths on average than the water droplets. This example shows that air bubbles generate absorbance peaks that are substantially different than water droplets. As such, systems herein can be configured to distinguish between water droplets and air bubbles and exclude the impact of air bubbles while measuring water concentration in fluid. Or exclude the impact of water drop concentration while measuring the air bubble concentration in a fluid.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A fluid system aeration detector comprising:
   an optical air bubble sensor, the optical air bubble sensor comprising
      a light source;
      a light detector; and
      a sensor controller;
   wherein the sensor controller is in signal communication with the light detector;
   wherein the sensor controller is configured to
      detect air bubbles based on the signals received from the light detector;
      estimate an amount of aeration of a fluid based on the detected air bubbles; and
      distinguish between air bubbles and water droplets in a fluid based on at least one of peak magnitude and peak width.

2. The fluid system aeration detector of claim 1, wherein the sensor controller is configured to distinguish between air bubbles and water droplets based on a ratio of peak magnitude to peak width.

3. The fluid system aeration detector of claim 1, wherein the sensor controller is configured to distinguish between air bubbles and water droplets based on peak magnitude.

4. The fluid system aeration detector of claim 1, wherein the sensor controller is configured to distinguish between air bubbles and water droplets based on a magnitude of a reflection peak prior to a peak resulting from absorbance, refraction, and/or scattering.

5. The fluid system aeration detector of claim 1, wherein the fluid system aeration detector is an on-vehicle sensing system.

6. The fluid system aeration detector of claim 1, wherein the optical air bubble sensor is configured to be disposed downstream from a filter and upstream from a fluid pump.

7. The fluid system aeration detector of claim 1, wherein the optical air bubble sensor is configured to be disposed within the fluid system at an area under vacuum pressure.

8. The fluid system aeration detector of claim 1, wherein the fluid system aeration detector is configured to initiate generation of an alert if a count of detected air bubbles over a period of time exceeds a threshold value.

9. The fluid system aeration detector of claim 1, wherein the fluid system aeration detector is configured to initiate generation of an alert if a detected volume of air bubbles exceeds a threshold value.

10. The fluid system aeration detector of claim 1, wherein the fluid system aeration detector is configured to track a count, a size distribution, and/or a volume of detected air bubbles over time.

11. A method of detecting fluid system aeration comprising:
   detecting air bubbles based on the signals received from a light detector; and
   distinguishing between air bubbles and water droplets in a fluid based on at least one of peak magnitude and peak width;
   estimating an amount of aeration of a fluid based on the detected air bubbles.

12. The method of claim 11, further comprising distinguishing between air bubbles and water droplets based on a ratio of peak magnitude to peak width.

13. A filter restriction sensing system comprising:
   an optical air bubble sensor, the optical air bubble sensor comprising
      a light source;
      a light detector; and
      a sensor controller;
   wherein the sensor controller is in signal communication with the light detector;
   wherein the sensor controller is configured to
      evaluate signals received from the light detector;
      detect air bubbles based on the signals received from the light detector;
      generate an estimate of a restriction level of a liquid filter upstream from the light detector based on the detected air bubbles; and distinguish between air bubbles and water droplets in a fluid based on at least one of peak magnitude and peak width.

14. The filter restriction sensing system of claim 13, wherein the sensor controller is configured to distinguish between air bubbles and water droplets based on a ratio of peak magnitude to peak width.

15. The filter restriction sensing system of claim 13, wherein the filter restriction sensing system is configured to generate an estimate of a restriction level of a fluid filter upstream from the light detector based on one or more properties of detected air bubbles; and the properties of detected air bubbles comprising at least one selected from the group consisting of average air bubble size, maximum air bubble size, counts of air bubbles, and air bubble volume as a percentage of total fluid volume.

16. The filter restriction sensing system of claim 15, wherein the filter restriction sensing system is further configured to generate the estimate of a restriction level using a fluid flow rate through the filter.

* * * * *